United States Patent
Lewis, III et al.

(10) Patent No.: US 6,386,038 B1
(45) Date of Patent: May 14, 2002

(54) ACOUSTIC APPARATUS AND INSPECTION METHODS

(76) Inventors: Carl Edwin Lewis, III, 3419 Viscount Dr., Arlington, TX (US) 76016; Daric William Escher, 7509 Logan Dr. SW., Huntsville, AL (US) 35802

(*) Notice: Subject to any disclaimer, the term of this patent is extended or adjusted under 35 U.S.C. 154(b) by 0 days.

(21) Appl. No.: 09/449,228

(22) Filed: Nov. 24, 1999

(51) Int. Cl.[7] .................................................. G01H 1/00
(52) U.S. Cl. .............................. 73/587; 73/588; 702/39
(58) Field of Search .......................... 73/570, 579, 582, 73/584, 587, 588, 596, 597, 598, 599, 600, 602, 606, 760, 788; 702/35, 36, 39; 340/665, 666, 669

(56) References Cited

U.S. PATENT DOCUMENTS

| | | | |
|---|---|---|---|
| 4,901,575 A | * 2/1990 | Bobannan et al. | 73/587 |
| 4,962,668 A | * 10/1990 | Preston et al. | 73/784 |
| 4,979,124 A | * 12/1990 | Sachse et al. | 73/587 |
| 5,270,950 A | * 12/1993 | Cowley et al. | 73/587 |
| 5,293,555 A | * 3/1994 | Anthony | 73/587 |
| 5,526,694 A | * 6/1996 | McEachern et al. | 73/587 |
| 5,533,383 A | * 7/1996 | Greene et al. | 73/40.5 |
| 6,065,342 A | * 5/2000 | Kerr et al. | 73/587 |

* cited by examiner

Primary Examiner—Richard A. Moller
(74) Attorney, Agent, or Firm—Eric P. Schellin

(57) ABSTRACT

The invented apparatus includes at least one acoustic sensor, a mapping unit, a controller, and a transducer. The sensor is coupled to an object to be inspected for damage, and generates a sensed signal based on acoustic signal occurring in the object under an applied load, which signal may or may not be the sound of damage occurring in the object. The mapping unit is coupled to receive the sensed signal from the sensor, and generates damage data based thereon. The controller is coupled to receive the damage data from the mapping unit. Initially, the apparatus is in a passive mode in which the apparatus senses an acoustic signal from the object. If the damage data indicates that the object has incurred possible damage in the passive mode, the controller switches to active mode and outputs induced signal data. The transducer is coupled to the object as well as the controller, and induces acoustic signal in the object, based on the induced signal data. The induced acoustic signal is detected by the sensor, mapped by the mapping unit, and supplied as damage data to the controller, after which the controller returns the apparatus to passive mode. If the damage data resulting from the induced acoustic signal indicates that the object has incurred actual damage, the controller can generate an alarm, a display of the damage, and/or store the damage data in a memory to provide a record of damage incurred by the object. The invention also includes related methods.

70 Claims, 13 Drawing Sheets

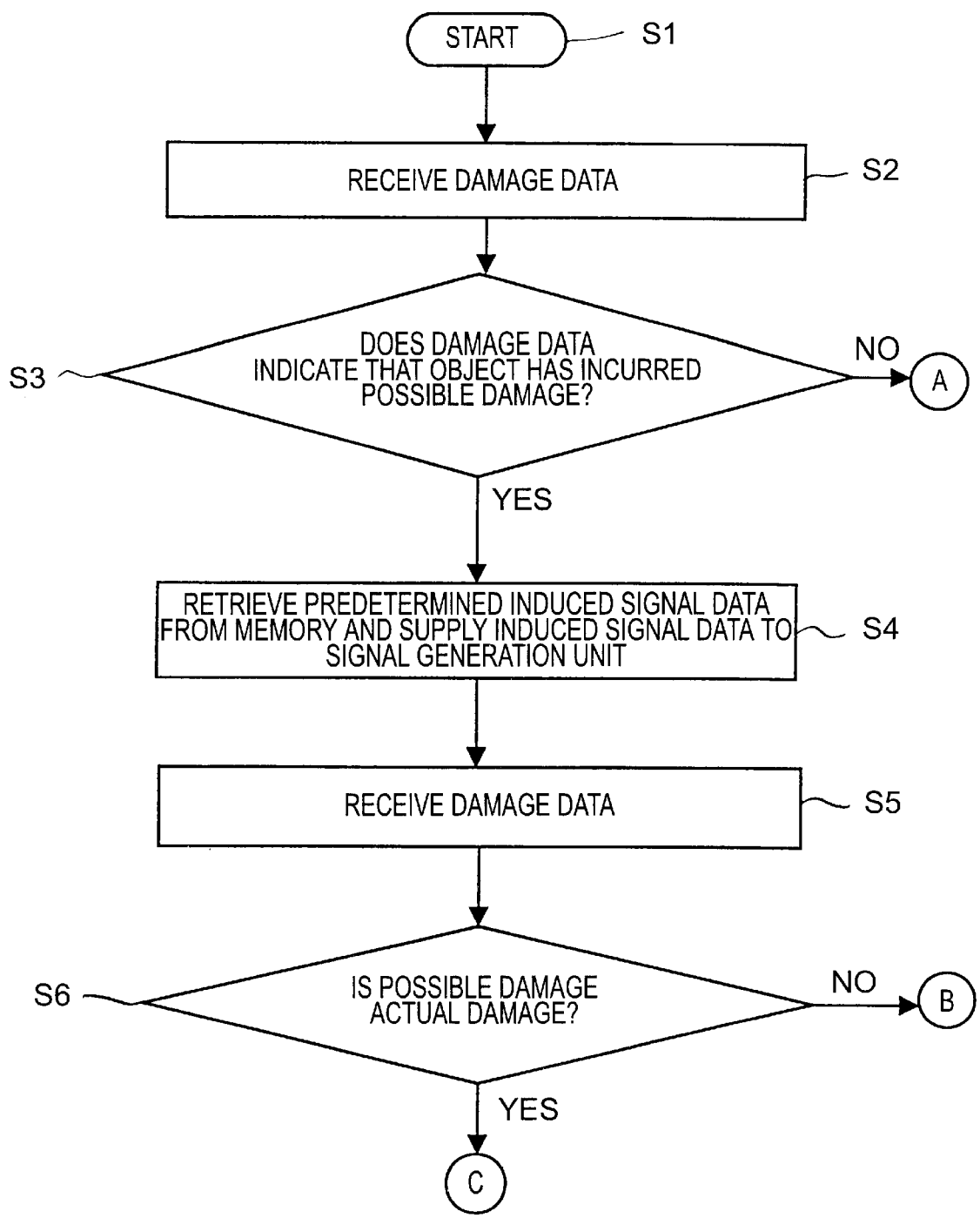

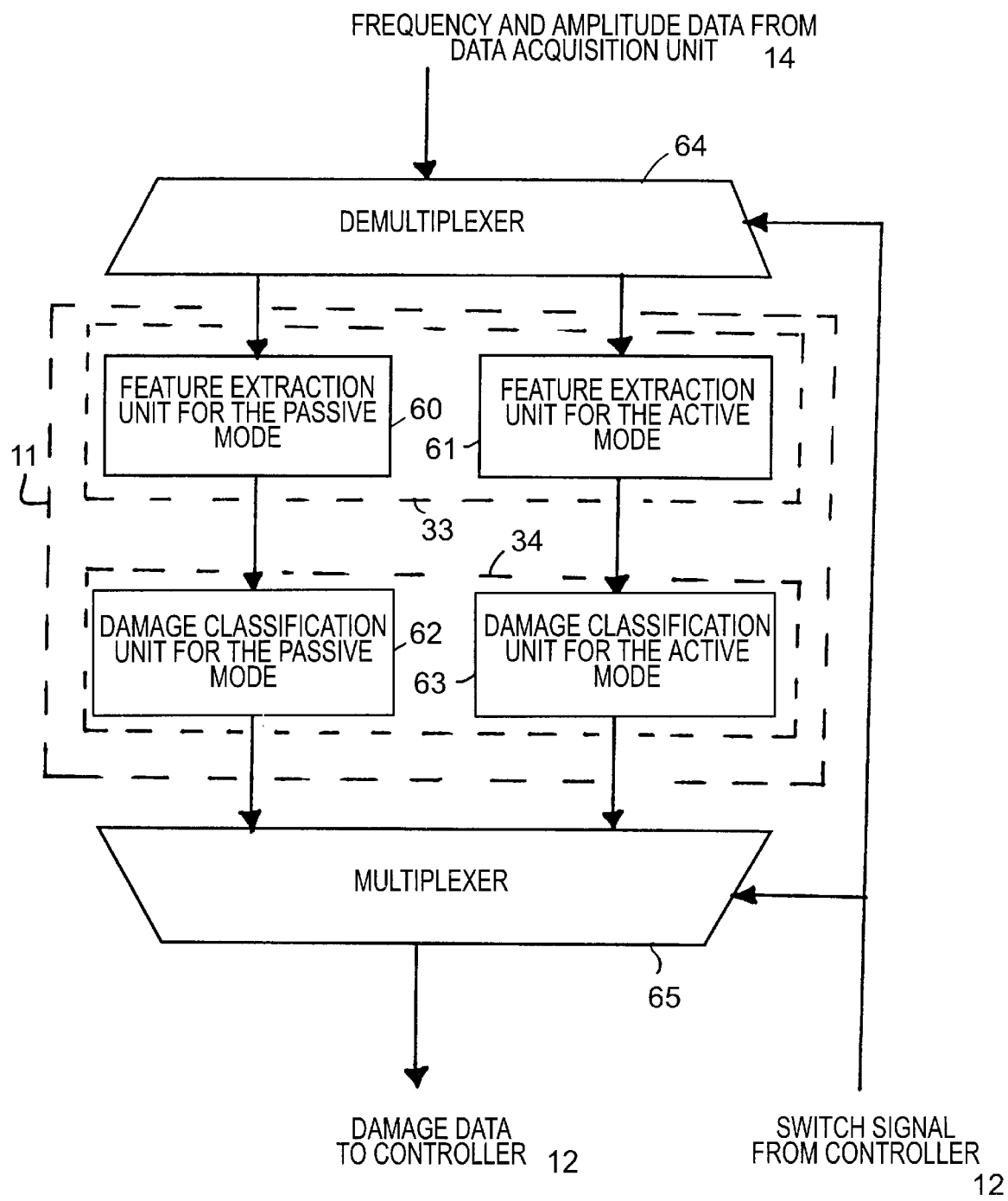

ACOUSTIC APPARATUS AND INSPECTION METHODS

FIELD OF THE INVENTION

1. Background of the Invention

The invented apparatus and methods pertain to acoustic inspection of an object such as, but not limited to, a part for an aircraft or other vehicle, to determine whether an object has incurred damage under an applied load, as well as the location and extent of any such damage. The invented apparatus and method can be used in the field of destructive or non-destructive stress testing of an object to determine whether the object is suitable for use in a particular application, for example. In addition, the invented apparatus and method can distinguish and categorize different types of damage to an object, as well as their relationship to the degree and manner in which a load is applied to the object.

2. Description of the Related Art

Acoustic emission (AE) testing uses an acoustic sensor to detect sound emitted by the occurrence of damage in an object subjected to an applied load. The sensor's output is analyzed to distinguish acoustic signals associated with background noise from acoustic signals related to damage of the object, such as sound emitted by the breaking of the object's materials under the applied load. By monitoring the acoustic signals emitted by the object under the applied load, much information can be obtained regarding the object's structural integrity and capability to withstand stresses in a particular application. However, AE testing is purely passive in nature, and because acoustic events may be indistinguishable as resulting from noise or damage, AE systems are incapable in some circumstances of capturing valuable or essential information regarding the true condition of the object.

Acousto-ultrasound (AU) testing uses a transducer to induce acoustic signals in an object as well as a sensor to detect the induced acoustic signals. After traveling through the object, the induced acoustic signals are detected by one or more sensors and are used to determine whether the object has incurred damage under an applied load. If an object has incurred damage, the induced acoustic signals will be disturbed in a manner which permits detection of the damage. AU testing provides a significant advantage in that it permits an object to be probed for the presence of damage. However, in applications in which it is desired to detect damage in an object that may occur at some indefinite time in the future, the AU system's power supply (e.g., a battery) may become exhausted through continuous use, or the AU system's components (e.g., the transducer or sensor) may wear out before the end of the object's useful life. It would be desirable to provide an apparatus and methods which can effectively detect damage in an object although such damage may occur at some indefinite time in the future.

Another problem related to this invention pertains to the detection of different categories of damage that can occur in an object. For example, composite materials are made of two or more materials that are integrated together, and they can be damaged under an applied load by failure of any one or some combination of its materials. It would be desirable to distinguish different categories of damage occurring in an object composed of composite or non- homogeneous materials, for example, to provide greater understanding of how the object is damaged under an applied load so that the object can configured and used in a relatively advantageous manner for a particular application.

Another problem related to this invention is that the acoustic behavior of an object changes as the object undergoes damage, so the sounds emitted by the occurrence of the same class of damage will change depending upon the amount of damage incurred by the object. The relationship between acoustic behavior and the amount of damage incurred is very difficult to ascertain and program into an AE or AU system, if it can be determined at all. It would be desirable to provide an apparatus and method in which acoustic signals resulting from damage can be readily determined without the need to determine relatively complex, non-linear relationships between such signals and the amount of damage incurred by the object.

SUMMARY OF THE INVENTION

The invented apparatus and methods have as their objects to overcome the above-stated problems with previous devices and techniques, and do in fact overcome such problems and provide significant advantages over the prior art.

The invented apparatus has a passive mode of operation in which the apparatus "listens" to sound emitted by the object to detect an acoustic signal that could possibly be the result of damage. Upon detecting such an acoustic signal, the apparatus switches to an active mode to probe the object with an induced acoustic signal to determine whether the sensed acoustic signal was the result of actual damage or is instead not the result of any damage. After making this determination, the apparatus can return to the passive mode to permit continuous monitoring of the object. Because the apparatus is normally in a passive mode of operation, it does not overuse its elements or prematurely exhaust its power supply as do previous apparatuses of this nature. In addition, the ability of the apparatus to actively probe the object permits the apparatus to accurately distinguish the sound of object damage from ambient noise.

The apparatus can include at least one sensor, a mapping unit, a controller, and at least one transducer. The sensor is mounted to sense an acoustic signal from the object, and generates a signal indicative of such signal. The mapping unit is coupled to receive the sensed signal from the sensor, and generates damage data based on the sensed signal. In the passive mode of operation, the mapping unit generates the damage data to indicate whether or not the object has incurred possible damage or conversely no damage, based on the sensed signal. The controller is coupled to receive the damage data from the mapping unit. If the damage data indicates that the object has incurred no damage, the controller maintains the apparatus in the passive mode. If the damage data indicates possible damage to the object, the controller switches the apparatus from the passive mode to the active mode by generating and outputting induced signal data. The transducer is mounted to the object and coupled to the controller, and induces acoustic signal in the object, based on the induced signal data. In the active mode, the induced acoustic signal is sensed by the sensor after traveling through at least the portion of the object that has incurred possible damage. The sensor generates the sensed signal that is indicative of the induced acoustic signal received by the sensor, and outputs the sensed signal to the mapping unit. In the active mode, the mapping unit generates damage data indicative of whether the object has incurred actual damage, or conversely, no damage, based on the sensed signal. The controller receives the damage data indicative of whether the object has incurred actual damage, and thereafter switches the apparatus from active mode to passive mode.

The apparatus can include a display unit coupled to the controller, that the controller uses to generate a display for a user, based on the damage data. The apparatus can also include a memory in which the controller stores the damage data for later reference or to provide a record of the damage incurred by the object under an applied load, for example. The apparatus can also include an alarm unit coupled to the controller, and the controller can generate an alarm signal, based on the damage data, to indicate to a user that the object has been damaged or that the object has been damaged beyond a predetermined limit. The mapping unit can also be such as to classify damage data in different categories. For example, if the object is a composite material, the mapping unit can classify the damage as fiber damage, fiber-matrix interface damage, fiber-matrix debonding, matrix damage such as cracking, fatigue or failure, or may even classify damage to particular localized portions or layers of the object.

A first method in accordance with this invention includes sensing at least one acoustic signal occurring in an object under an applied load, and determining whether the object has incurred possible damage under the applied load, based on the acoustic signal sensed in the sensing step. The method can also include inducing at least one acoustic signal in the object if the determining step indicates that the object has incurred possible damage. The method can also include sensing the induced acoustic signal from the object, and a step of determining whether the possible damage is actual damage of the object, based on the induced acoustic signal sensed in the later sensing step.

A second method in accordance with this invention includes sensing at least one acoustic signal in an object subjected to an applied load to generate a sensed signal, extracting at least one feature from the sensed signal, and classifying the sensed signal as pertaining to one of a plurality of categories including at least damage and no damage, based on the feature.

These together with other features and advantages, which will become subsequently apparent, reside in the details of construction and operation as more fully hereinafter described and claimed, reference being made to the accompanying drawings, forming a part hereof wherein like numerals refer to like parts throughout the several views.

BRIEF DESCRIPTION OF THE DRAWINGS

FIGS. 9A–9D are flow charts of processing performed by a controller of the invented apparatus; and FIG. 10 is a block diagram of a variation of the mapping unit of the invented apparatus.

DESCRIPTION OF THE PREFERRED EMBODIMENTS

As used herein, the following terms have the following definitions:

"Composite material" is a combination of two or more materials (reinforcing elements, fillers, and composite matrix binder), differing in form or composition on a macro scale. The constituents retain their identities, that is, they do not dissolve or merge completely into one another although they act in concert. Normally, the components can be physically identified and exhibit an interface between one another. ASM Materials Engineering Dictionary, 1992.

"Coupled" in an electronic sense refers to joining electronic components together with a conductive line such as a wire or cable, or by transmission of signals through air, for example. "Coupled" in a mechanical sense refers to joining two or more objects together by an adhesive, or through mechanical devices such as a clamp or the like.

"Fiber" is an elongated strand of material, such as silicon carbide (SiC) or graphite (C) fibers.

"Load" refers to a force applied to an object, which can be torsional, compressive, tensile, vibrational or thermally induced.

"Matrix" refers to the main portion or mass of a composite material such as compressed layers of metal foil such as titanium or aluminum, in which fibers or other composite components are fixed. The matrix can alternatively include powdered metal, metal fibers, metal-coated fibers, plastics, ceramics, and polymers, "Monolithic" refers to uniform material of a single element, or alloy or compound.

1. A Composite Object

Figure 1:
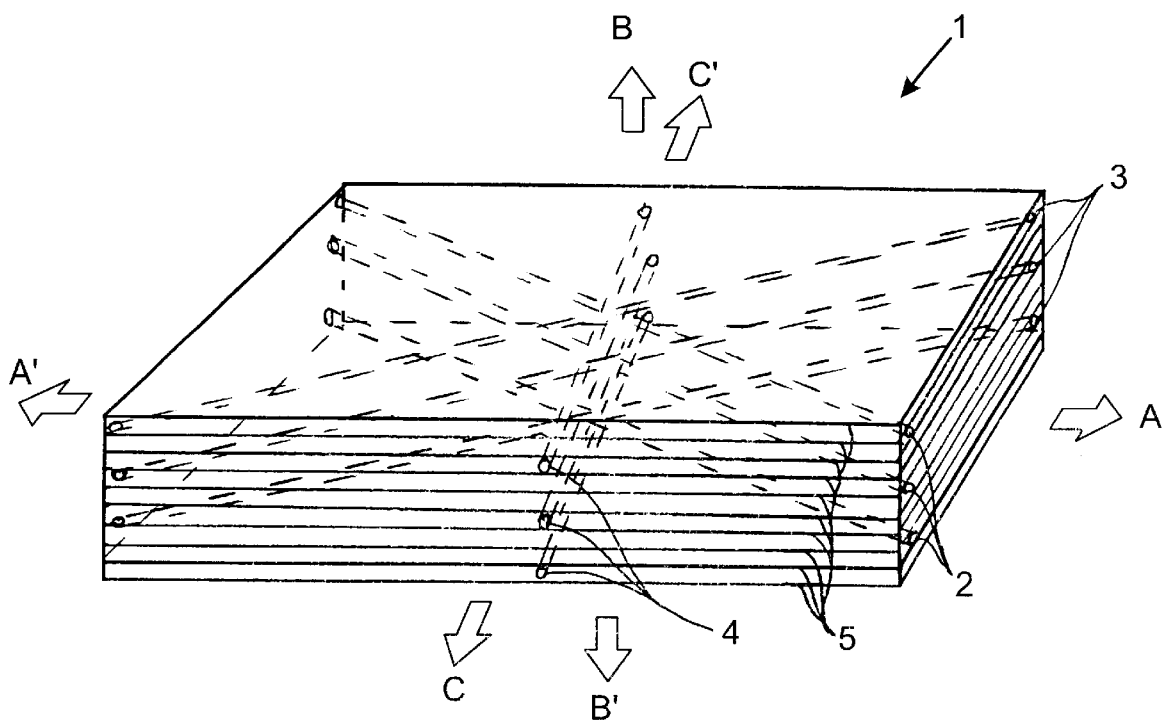
FIG. 1 is a perspective view of an object composed of a composite material, that can be inspected with the invented apparatus.

In FIG. 1, an object 1 is shown. The object 1 can be inspected or stress-tested, for example, with the invented apparatus and methods. The object 1 can be an exterior panel of an aircraft, rocket or other vehicle, for example. The invented apparatus and methods can be applied to inspect the object 1 for damage which may have been incurred due to improper manufacture, a load applied by air during flight, by impact with another object, for example, or by another form of load applied to the object. In the example of FIG. 1, the object 1 is implemented as a composite material that includes fibers 2, 3, 4 and matrix layers 5 in which the fibers are positioned. For example, the fibers 2, 3, 4 can be composed of elongated strands of silicon carbide (SiC), and the matrix can be formed of metal foil layers, metal powders, metal-coated fibers, or metal fibers (not specifically shown) such as titanium or aluminum, that are compressed together. Due to the malleability of the foil, the fibers 2 become embedded in an approximately uniform metal matrix upon compressing the foil layers together. The object 1 could be composed of a composite material such as graphite fibers in an epoxy matrix that is cured to fix the fibers in position. The object 1 could also be composed of other composite or monolithic materials.

In FIG. 1, the fibers 2, 3, 4 are arranged in different orientations in the matrix 5. Specifically, the fibers 2, 3, 4 are arranged in respective layers that are parallel to the major surfaces of the object 1, and are arranged transversely relative to each other. Although only one fiber 2, 3, 4 is shown per fiber layer to reduce complexity of the drawing, there are preferably a plurality of fibers 2, 3, 4 per inch. In the exemplary embodiment of FIG. 1, the fibers are positioned in a spaced, parallel relationship so that the fibers of a layer are unidirectional. However, there is no general requirement that such fibers be arranged unidirectionally, and they could be positioned in a transverse arrangement as is the case with graphite cloth or polymeric materials such as nylon which can have fiber layers oriented at 0 degrees, ±45 degrees, and/or 90 degrees relative to one another. The fibers could be arranged at any other transverse angle as well. The thickness of the layers 5 can be on the order of a millimeter or less before compressing the layers together.

The manner in which the object 1 is damaged under an applied load depends on the direction and magnitude of the applied load. As shown in FIG. 1, if the object 1 is subjected to tensile stress in the direction A–A', the fibers 2, 3 will be subjected to a relatively large degree of stress whereas fibers 4 will be subjected to comparatively less stress, so it would be expected that the fibers 2, 3 will incur damage before the fibers 4 under this particular load. If the object 1 is subjected to tensile stress in the direction B–B', the fibers 2, 3, 4 will be subjected to relatively little stress under this particular load. If the object 1 is subjected to a tensile stress in the direction C–C', the fibers 4 will be subjected to a relatively high degree of stress, and the fibers 2, 3 will be subjected to less stress than the fibers 4. The matrix layers 5 will be subjected to relatively large tensile stress if pulled in the directions A–A', C–C', and will tend to pull apart if stressed in the direction B–B'. Therefore, the fibers 2, 3, 4 and the matrix 5 will tend to be damaged in ways that are highly dependent upon the direction in which stress is applied to the object 1. Moreover, the sound or acoustic signals emitted by different types of damage occurring in the object 1 are distinguishable and indicative of the type of damage taking place in the object. For example, the sound of the fibers 2, 3, 4 breaking is distinguishable relative to sounds emitted by damage to the matrix 5. More specifically, the sound of a fiber break tends to have a relatively low frequency content, but high amplitude. Conversely, matrix damage tends to have relatively high-frequency, but low amplitude. In addition, the acoustic signal associated with fiber damage can vary greatly in amplitude and frequency content depending upon the direction of the applied load and the particular fiber or matrix layer that fails. In addition, particular layers will fail and emit acoustic signals indicative thereof, before other layers fail under an applied load. The acoustic behavior of the object 1 is thus highly indicative of the damage the object undergoes as it is subjected to stress. The invented apparatus can be used to not only distinguish the sound of an object undergoing damage from background noise, but can also if desired be used to distinguish different kinds of damage occurring in an object. For example, the invented apparatus can be used to distinguish sounds emanating from the object under transverse loads such as fiber-matrix debonding or matrix failure.

Although the object 1 of FIG. 1 is a composite material, the invented apparatus and methods can be applied to analyze an object that is monolithic. For example, such materials could include titanium, aluminum or other metals, metal alloys, or polymer materials, for example. In monolithic materials, the types of damage incurred under an applied load can be classified as surface cracking, necking, fatigue, or cracking, for example.

2. An Embodiment of the Invented Apparatus

Figure 2:
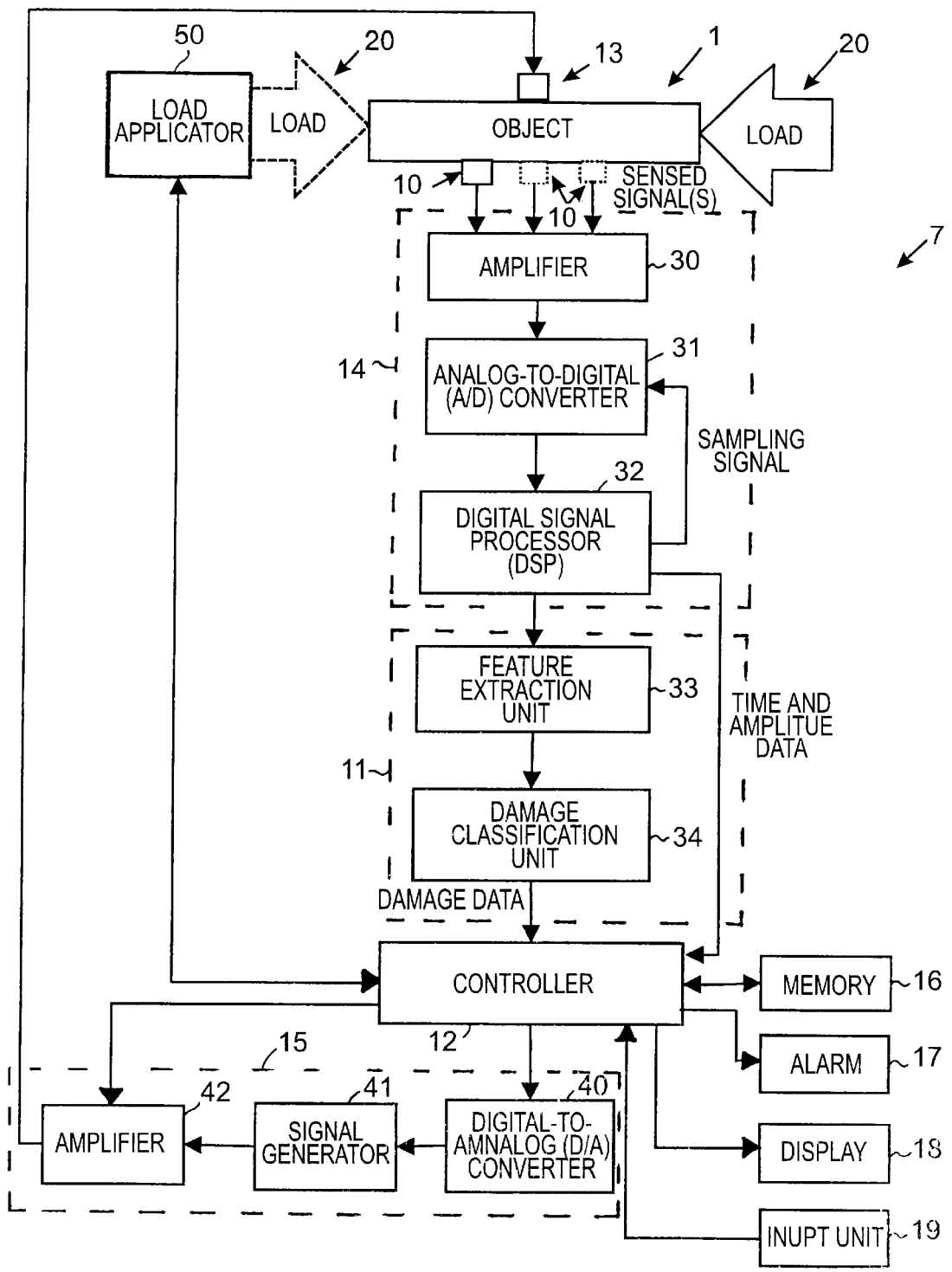
FIG. 2 is a block diagram of an embodiment of the invented apparatus.

In FIG. 2, the invented apparatus 7 generally includes at least one sensor 10, a mapping unit 11, a controller 12, and a transducer 13. The apparatus can also include a data acquisition unit 14, an induced signal generation unit 15, a memory 16, an alarm unit 17, a display unit 18, and an input unit 19.

The sensor(s) 10 is mounted to the object 1 to be inspected for damage as a result of an applied load 20. The sensor(s) 10 can be a microphone(s) sensitive to acoustic signal in the range from one kilohertz (1 kHz) to hundreds of megahertz (100s MHz). The sensor(s) 10 can be, for example, a Hi-Temp Model D9215 acoustic sensor commercially available from Physical Acoustics Corporation™. The sensor(s) 10 can be mounted to the object 1 with a coupling adhesive suitable for the operational environment (e.g., in high-temperature environments, of course, adhesives capable of withstanding such temperatures should be used). If the object is a composite material, a plurality of sensor(s) 10 can be attached to the object on the top and/or bottom major surfaces of the object to detect acoustic signal from damage occurring thereto. The number of sensor(s) 10 used and their relative positioning depends upon numerous factors, such as the configuration, size and degree of acoustic attenuation of the materials composing the object 1, as well as whether the apparatus 7 is to have the capability to determine the location of damage within the object 1. More specifically, each sensor will be capable of detecting acoustic signal over a limited coverage area of the object, so a sufficient number of sensor(s) 10 should be used to provide complete coverage to detect acoustic signals emitted by damage occurring at any portion of the object 1. In addition, if the apparatus 7 is to have the capability to determine the location of damage to the object 1, at least three spaced sensors 10 should be used to provide the capability to triangulate to the source of the damage based on the relative time of arrival of the acoustic signal from the point of damage within the object 1.

The sensor(s) 10 generates an electric sensed signal based on the acoustic signal received from the object. The sensor (s) 10 is preferably coupled to output its sensed signal to the data acquisition unit 14. The data acquisition unit 14 can be a device such as the AMSY4 Acoustic Emission System™ commercially available from Vallen™ Ltd. of Icking, Germany. The data acquisition system 14 can include an amplifier 30, an analog-to-digital (A/D) converter 31, and a digital signal processor (DSP) 32. The amplifier 30 is coupled to receive the sensed signal from the sensor(s) 10, and generates an amplified signal(s) based thereon. The A/D converter 31 is coupled to receive the amplified signal(s) and also a sampling signal generated by the DSP 32. The DSP 32 activates the sampling signal at regular time increments to cause the A/D converter 31 to latch or capture samples of the amplitudes of the amplified signal(s), and converts the amplitude samples of such signal(s) from analog into digital form. The amplitudes and the respective time increments in which they were sampled may be referred to herein as 'amplitude and time data'. To satisfy the Nyquist criterion, the sampling rate should be performed at a rate greater than twice the highest frequency of interest in the acoustic signal, or in other words, greater than one gigahertz (1 GHz) assuming that the highest frequency of interest is no more than five-hundred megahertz (500 MHz). The DSP 32 transforms the time and amplitude data in time domain, to frequency and amplitude data in frequency domain by the performance of a Fast Fourier Transform (FFT) or other transformation. The DSP 32, or more generally the data acquisition unit 14, is coupled to output the frequency and amplitude data to the mapping unit 11.

The mapping unit 11 is coupled to receive the frequency and amplitude data from the data acquisition unit 14, and generates damage data, based on the frequency and amplitude data. In the apparatus' passive mode, the mapping unit 11 maps the frequency and time data to damage data indicative of whether the object has incurred possible damage or no damage. In addition, the mapping unit 11 can be such as to further categorize the frequency and amplitude data into different possible damage categories. If the object 1 is a composite material, such possible damage categories can include fiber damage, fiber-matrix interface damage, fiber-matrix debonding, matrix damage, or even damage to particular matrix or fiber layers. If the object 1 is monolithic, such possible damage categories can include surface cracking, necking, fatigue, and cracking. In the apparatus' active mode, the mapping unit 11 maps the frequency and time data to damage data indicative of whether the object has incurred actual damage or no damage. In addition, the mapping unit 11 implemented to further categorize the frequency and amplitude data into different actual damage categories. If the object 1 is a composite material, these actual damage categories can include fiber damage, fiber-matrix interface damage, fiber-matrix debonding, matrix damage, or even damage to particular matrix or fiber layers. If the object 1 is monolithic, these actual damage categories can include surface cracking, necking, fatigue, and cracking.

The mapping unit 11 is preferably implemented as a learning system which can determine the mapping of the frequency and amplitude data to the correct classification as damage, optionally of a particular type, or no damage. The use of a learning system is particularly advantageous because it is well-suited to handling the situation in which there may be no ascertainable function relating sounds emitted by the object and the classification of those sounds as pertaining to damage or not damage (e.g., background noise). In other words, a learning system has the capability to learn a mapping of the frequency and amplitude data from the data acquisition unit 14 to the classification of the frequency and amplitude data for output to the controller 12, with little or no understanding of the underlying processes relating the frequency and amplitude data from the acoustic signal, to the damage data indicative of possible or no damage in passive mode, or actual damage or no damage in active mode.

The mapping unit 11 can be implemented with a learning system such as a processor coupled to a memory, a microcontroller coupled to a device sold under the trademark NNP® that is commercially available from Accurate Automation™ Corporation, of Chattanooga, Tenn., a fuzzy logic processor, or other device. Preferably, the learning system includes a feature extraction unit 33 and a damage classification unit 34. The feature extraction unit 33 is coupled to receive the frequency and amplitude data from the DSP 32, and extracts one or more features from such data which are indicative of possible damage or no damage in the passive mode, and actual damage and no damage in the active mode, and outputs such features to the damage classification unit 34. The feature extraction unit 33 can further generate the features so as to classify the possible damage in the passive mode or actual damage in the active mode into more specific damage categories. If the object 1 is composite, the features can classify possible or actual damage as fiber damage, fiber-matrix interface damage, fiber-matrix debonding, and/or matrix damage such as cracking, fatigue or failure, respectively. The feature extraction unit 33 can further classify the damage by fiber or matrix layer. If the object 1 is monolithic, the features can classify possible or actual damage as surface cracking, necking, fatigue or cracking. The resulting features are output from the feature extraction unit 33 to the damage classification unit 34. The feature extraction unit 33 can be implemented as a neural network that uses a self-organizing feature map (SOM), as described, for example, in "Neural Networks: A Comprehensive Foundation," Second Edition, authored by Simon Haykin, Copyright © 1999 by Prentice-Hall, Inc. (see generally Chapter 9; FIG. 9.13). The damage classification unit 34 is coupled to receive the features from the feature extraction unit 34, and classifies the features into one of the categories of possible damage or no damage in passive mode, and actual damage or no damage in active mode, and outputs such classification as damage data. As previously described, the damage categories in both passive and active modes can be further divided into more specific damage categories to distinguish fiber damage, fiber-matrix interface damage, fiber-matrix debonding, matrix damage if the object 1 is composed of a composite material, or can further distinguish damage to different matrix or fiber layers, or portions, of the object 1. If the object 1 is monolithic, the damage categories in both passive and active modes can be further divided into more specific damage categories to distinguish surface cracking, necking, fatigue, and cracking. The damage classification unit 34 can be implemented as a learning vector quantizer with a supervised learning scheme to provide an adaptive classification of the features (see, e.g., FIG. 9.13 of the above-stated text). For example, this capability permits the damage classification unit 34 to readily adjust its damage classifications or categories for different types of objects, or for changes in acoustic signal caused by different degrees of object damage. The learning vector quantizer can be implemented as a processor coupled to a memory, that is further coupled to receive the feature(s) from the damage classification unit 34. Such processor can be programmed to perform the adaptive classification scheme and output the damage class or category determined by the processor using the feature(s), as damage data to the controller 12. For example, the adaptive classification scheme can use Voronoi vectors as mentioned in the above-stated text, which are adjusted to adapt the damage classifications or categories, based on the feature data. The damage classification unit 34 generates the damage data based on the feature data, and outputs the resulting damage data to the controller 12.

In FIG. 2, the controller 12 is coupled to receive the damage data from the damage classification unit 34, or more generally, the mapping unit 11. The controller 12 can also be coupled to receive the time and amplitude data from the DSP 32, or more generally, from the data acquisition unit 14. The controller 12 can be implemented as a microprocessor such as a Pentium® II commercially available from Intel® Corporation, Palo Alto, Calif., for example, or comparable microprocessor. The controller 12 is coupled to a memory unit 16 and can store the damage data in correspondence with respective time and amplitude data therein. The memory 16 can implemented as a random access memory (RAM), for example, with sufficient memory space to store the controller's operating program as well as the damage data, and preferably also time data and amplitude data, and various other data, stored in the memory by the controller 12.

The controller 12 is also coupled to the alarm unit 17. The alarm unit 17 can be a variety of conventional devices, such as a light- or sound-emitting device. Such device could be implemented as a light-emitting diode (LED), buzzer, speaker or the like. The controller 12 generates an alarm signal, based on the damage data. The controller 12 outputs the alarm signal to the alarm unit 17 to generate a visual and/or sonic alarm to a user of the apparatus to indicate that the object 1 has been damaged, or has been damaged beyond a predetermined limit. The controller 12 is coupled to the display unit 18. The display unit 18 can be one of a variety of devices such as a cathode-ray tube (CRT), a liquid crystal display (LCD), or other flat-panel display. The controller 12 can generate a display signal, based on the damage data, and optionally also based on the time data and amplitude data. The controller 12 supplies the display signal to the display unit 18 to generate a visual display.

In FIG. 2, the controller 12 is coupled to the signal generation unit 15. Initially, the controller 12 is in the passive mode of operation in which the controller monitors the object for damage data corresponding to sounds within the object that indicate possible damage to the object. After receiving the damage data from the mapping unit 11 which indicates that the object 1 has incurred possible damage, the controller 12 switches the apparatus 7 from passive mode to active mode, and supplies induced signal data to the signal generation unit 15. The signal generation unit 15 generates an induced acoustic signal, based on the induced signal data received from the controller 12. More specifically, the controller 12 retrieves induced signal data stored in the memory 16 before operation of the apparatus 7 via the input unit 19 and the controller, for example. The controller 12 supplies the retrieved induced signal data to the signal generation unit 15. The induced signal data can include predetermined data indicative of the frequency and amplitude for the acoustic signal to be induced in the object 1 by the apparatus 7. The frequency of the induced signal is generally desired to be in the range from one-kilohertz (1 kHz) to five-hundred kilohertz (500 kHz), although is not limited to this range. The frequency of the induced acoustic signal is also preferred to be such that it does not overlap frequencies significantly present as background noise or frequencies associated with object damage, or harmonics or beats thereof. The frequency of the induced signal is also preferred to be predetermined to be one that is not too high that it is unreasonably attenuated in the object 10 and thus cannot be detected by the sensor(s) 10. The amplitude of the induced signal is predetermined so that the sensor(s) 10 can readily detect the induced acoustic signal after traveling through the object 1.

The signal generation unit 15 is coupled to receive the induced signal data generated by the controller 12. The signal generation unit 15 can include a digital-to-analog (D/A) converter 40, a signal generator 41, and an amplifier 42, as shown in FIG. 2. The D/A converter 40 is coupled to receive the induced signal data that is indicative of the amplitude of the acoustic signal that is to be induced in the object 1, and converts the frequency data from digital form into an analog signal such as a voltage level, for example. The signal generator 41 is coupled to receive the analog signal from the D/A converter 40, and generates a signal whose frequency is dependent upon the analog signal from the D/A converter. The signal generator 41 can be one of numerous commercially available devices, such as a voltage-controlled crystal oscillator, timers, or other devices, optionally with frequency stabilization circuitry, for example. The amplifier 42 is coupled to receive the signal generated by the D/A converter 40, and is also coupled to receive the amplitude data of the induced signal data generated by the controller 12. The amplifier 42 generates an amplified signal, based on the signal generated by the signal generator 41 and the amplitude data. More specifically, the amplifier 42 amplifies the signal generated by the signal generator 42, by an amount determined by the amplitude data.

The transducer 13 is coupled to receive the signal from the amplifier 42 to the signal generation unit 15, and is mounted to the object 1 so as to permit transmission of acoustic signal generated by the transducer 13 into the object. The transducer can be mounted to the object 1 with the same adhesive substance, for example, as previously mentioned for use in mounting the sensor(s) 10 to the object 1. The transducer 13 can be an ultrasonic pulser such as the aforementioned Hi-Temp Model D9215 (this particular unit can function both as a sensor and as an ultrasonic pulser). The transducer 13 generates an acoustic signal in the object, based on the signal received from the amplifier 42 of the signal generation unit 15. The acoustic signal is modified by the presence of damage in the object 1, and received by the sensor(s) 10. The sensor(s) 10 generate respective sensed signal(s), based on the acoustic signal(s) received from the object, which are supplied to the data acquisition unit 14. The operation of the data acquisition unit 14 in the passive mode is similar to that in the active mode. In other words, the data acquisition unit 14 generates frequency and amplitude data, based on the sensed signal(s). The frequency and amplitude data are supplied to the mapping unit 11, or more specifically the feature extraction unit 33, which extracts one or more features from the frequency and amplitude data. The extracted feature(s) for the active mode can be the same as those extracted by the apparatus in the passive mode. The extracted feature(s) are supplied from the feature extraction unit 33 to the damage classification unit 34 for classification as damage data. More specifically, the damage classification unit 34 maps the extracted feature(s) into classifications or categories including at least actual damage to the object, and no actual damage to the object. The damage classification unit 34 can, if desirable for a particular application of the invented apparatus, map the extracted feature(s) so as to classify the actual damage in the active mode, into more specific actual damage categories. For example, if the object 1 is composite, the damage classification unit 34 can map the extracted feature(s) to indicate different classes of actual damage, such as fiber damage, fiber-matrix interface damage, fiber-matrix debonding, and/or matrix damage, or damage to different matrix or fiber layers or portions of the object. If the object 1 is monolithic, the damage classification unit 34 can map the extract features(s) to indicate different classes of actual damage such as surface cracking, necking, fatigue, and cracking. The damage classification unit 34 supplies the damage classification determined by its mapping to the controller 12 as damage data.

The controller 12 can store the damage data indicative of the actual damage incurred by the object 1 in the memory 16, optionally in correspondence with the time data from the data acquisition unit 14, to provide a record of actual damage incurred by the object 1. The controller 12 can also store the damage data in correspondence with the amplitude data for use by the controller in determining the severity of damage incurred by the object 1, for example. In addition, the controller 12 can increment a count of the total number of occurrences of damage incurred by the object 1, optionally for particular classes of damage, and can compare the count with a predetermined limit stored in the memory 16 via the input unit 19 prior to operation of the apparatus 7. If the controller 12 determines that the damage count exceeds the predetermined limit, the controller 12 can generate an alarm signal supplied to the alarm unit 17 to generate an alarm to alert the user that the object 1 has been damaged beyond the predetermined limit. In addition, if the apparatus 7 includes more than one sensor 10, the controller 12 can use the time and amplitude data from respective sensor(s) 10 to determine the relative time of arrival of the induced acoustic signal at the respective sensor(s). By predetermination of the relative position of the transducer 13 and the sensor(s) 10 and programming of this data into the controller 12 along with appropriate computational programs, the location of the actual damage within the object 1 can be determined by the controller 12 in a manner that is well-known (see, e.g., U.S. Pat. No. 4,535,629 issued to David W. Prine on Aug. 20, 1985, and U.S. Pat. No. 5,115,681 issued to Ahmed Bouheraoua et al. on May 26, 1992, which are incorporated herein by reference). After receiving the damage data in active mode, the controller 12 switches operation of the apparatus 7 to the passive mode and no longer outputs induced signal data to the signal generation unit 15. The controller 12 can switch from passive mode to active mode and back as often as necessary to detect and classify acoustic signal within the object 1.

In some applications such as stress testing of an object to determine whether it is capable of withstanding stresses expected in a particular operating environment, the apparatus 7 can be provided with the capability to load the object 1. More specifically, the apparatus 7 can include a load applicator 50 coupled to the controller 12. The load applicator 50 can include a loading rig such as an MTS™ closed-loop servo-hydraulic load frame in which the object 1 is mounted for compression, tensile or torsional loading. The controller 12 can increment the stress applied to the object 1 according to a predetermined load schedule, and control the load frame to change the stress applied to the object by the load frame during stress testing. For example, the controller 12 can be preprogrammed to stress the object 1 by increments of one kilopound per square inch (1 KSI) from one (1) KSI to one-hundred (100) KSI over a time period of approximately thirty (30) minutes, for example. Alternatively, the load applicator 50 can be implemented as a clam-shell testing furnace capable of temperature loading the object 1 by heating the object 1 from ambient temperature as high as 500° Celsius or more, for example. In this case, the controller 12 gradually increments the temperature applied to the object 1, for example, so as to heat the object from room temperature to five-hundred (500) degrees over a period of thirty (30) minutes. The above stress schedules are given by way of example and not limitation. The controller 12 can store the applied load data together with the damage data resulting therefrom, and also optionally the time, amplitude and damage position data, in the memory 16. The controller 12 can also retrieve such data for display on the display unit 18, in response to a user input command from the input unit 19, for example.

Figure 3:
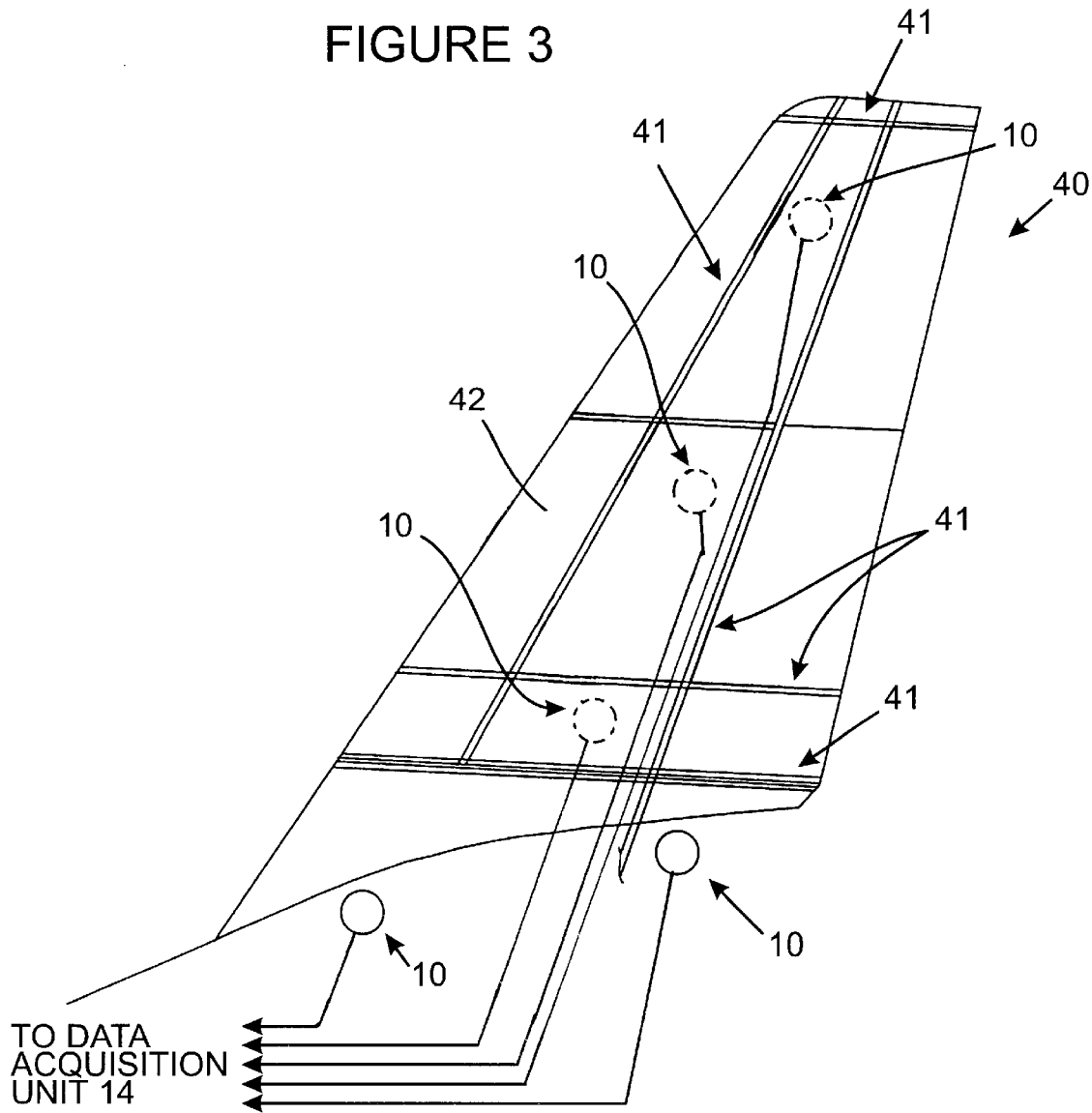
FIG. 3 is a partial cross-sectional view of an embodiment of a wing or stabilizer flight structure of the invented apparatus.

In FIG. 3, a flight structure 40 such as a wing or vertical or horizontal stabilizer of an aircraft, is shown. The flight structure 40 has structure 41 that supports aircraft skin 42. Sensors 10 are cemented to the undersurface of the skin 42 inside of the aircraft to sense acoustic signals from the structure 41 and/or skin 42. Based on acoustic signals from the structure and/or skin, optionally induced by transducer 13 (not shown in FIG. 3), the sensor(s) 10 generate respective signals supplied to the data acquisition unit 14 of the apparatus 7. The apparatus 7 can thus be used to determine whether the aircraft has incurred damage and can further classify such damage, as described above with respect to FIG. 1.

3. Basic Operation of the Invented Apparatus and First Method of the Invention The basic operation of the invented apparatus 7, as well as a first method of this invention, are now described with respect to FIG. 4. In step S1, the method of FIG. 4 begins. In step S2, the apparatus 7 performs a step of sensing acoustic signal(s) occurring in the object 1 under an applied load 20. In step S3, the apparatus 7 determines whether the object 1 has incurred possible damage, based on the sensed acoustic signal. If not, the method proceeds to step S4 in which the apparatus generates a signal (i.e. damage data) indicative of the fact that the object has incurred no damage, and thereafter, processing terminates in step S10. If, on the other hand, the determination in step S3 is affirmative, the method proceeds to step S5 in which the apparatus 7 induces an acoustic signal in the object 1 to probe the possible damage therein. In step S6, the apparatus 7 senses the induced acoustic signal from the object 1. In step S7, the apparatus 7 determines whether the possible damage is actual damage, based on the induced acoustic signal sensed in step S6. If so, in step S8, the apparatus 7 generates a signal (i.e. damage data) indicative of the fact that the signal has incurred actual damage, and in step S10, the method performed by the apparatus 7 terminates. On the other hand, if the apparatus 7 determines that the object has incurred no damage in step S7, the apparatus 7 generates a signal (i.e. damage data) indicating that the object 1 has incurred no damage in step S9, and the method ends in step S10. The method of FIG. 4 can be repeated, for example, at intervals of one millisecond or less, to permit any damage that may be incurred by the object to be detected. The apparatus 7 can use the damage data generated by the method of FIG. 4 for storage in the memory 16 along with other data, for generation of an alarm via alarm unit 17, or for generation of a display 18, for example, as previously described. In the foregoing method, steps S1–S4 correspond to the apparatus' passive mode of operation, and steps S5–S9 correspond to the apparatus' active mode. After performance of steps S5–S9, in step S10, the apparatus 7 returns to passive mode and discontinues the induction of induced acoustic signal in the object 1.

4. Training the Mapping Unit

Figure 5:
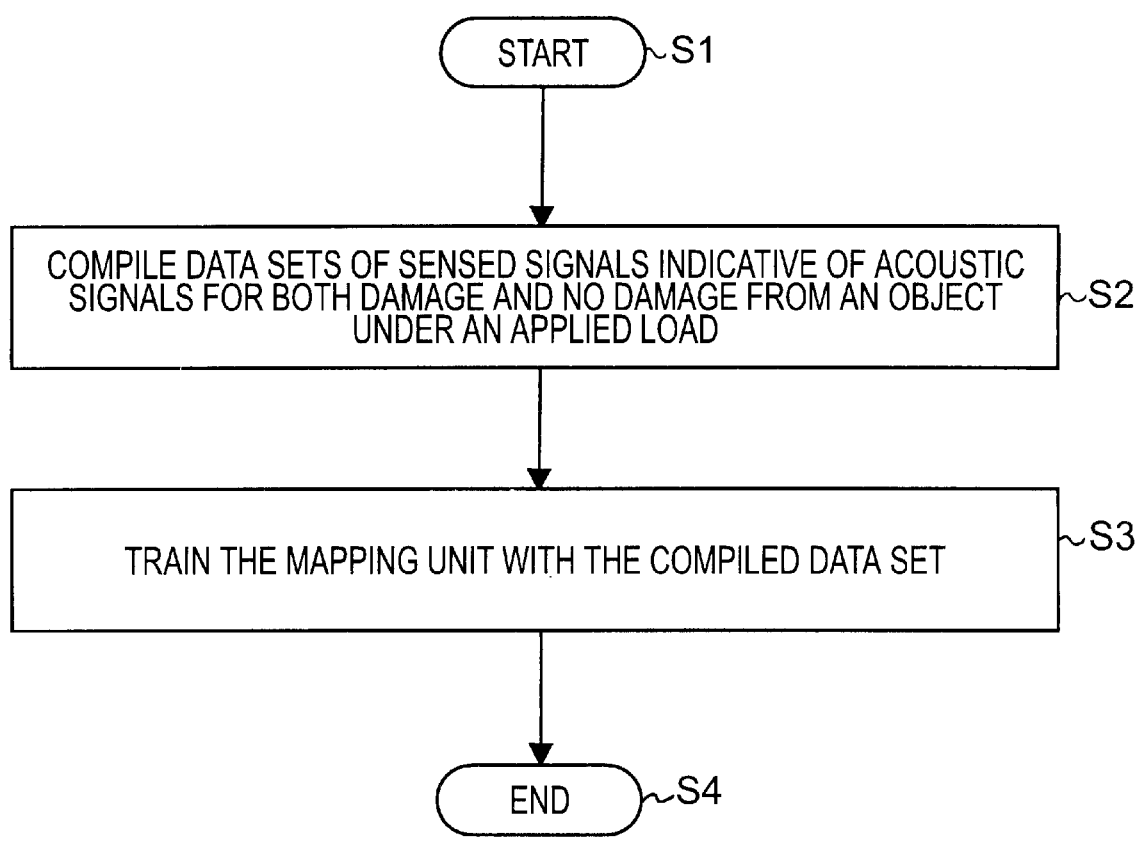
FIG. 5 is a flow chart of a method for training a learning system of the mapping unit of the invented apparatus.

The mapping unit 11 is preferably trained before operation of the invented apparatus to permit the apparatus 7 to effectively classify sensed acoustic signals into corresponding damage classifications for output as damage data. As shown in FIG. 5, training of the mapping unit 11 begins in step S1. In step S2, a data set is compiled of frequency and amplitude data for sensed signals resulting from acoustic signals from the object 1 and the corresponding classifications for the sensed signals including at least the classifications of damage to the object and no damage to the object, and possibly further divided and distinguished into more specific damage categories. For example, if the object 1 is composite, the data set can be divided to distinguish fiber damage, fiber-matrix interface damage, fiber-matrix debonding, matrix damage, or to further distinguish damage to different matrix or fiber layers, or portions, of the object 1. If the object 1 is monolithic, the data set can be divided to distinguish damage such as surface cracking, necking, fatigue, or cracking. Further, the mapping unit 11 can be trained with a data set compiled from frequency and amplitude data derived from both passively-sensed and actively-induced acoustic signals, or can be divided into two parts, one for passive mode and the other for active mode in which two data sets of acoustic signals sensed in passive mode and induced and sensed from the object in active mode, are compiled for training the mapping unit 11 in step S2 of FIG. 5 (the later variation will be addressed in further detail with respect to FIG. 10). Importantly, the compiled data set should include several acoustic signals for each class of damage desired to be distinguished by the mapping unit 11, including acoustic signals resulting from all categories of damage that are desired to be detected as well as background or ambient noise present under a condition in which the object has incurred no damage. In step S3 of FIG. 5, the mapping unit 11 is trained with the compiled data set to properly classify the data sets to damage data indicative of proper damage or no damage categories. In step S4, the method of FIG. 5 ends.

5. Basic Operation of the Sensor(s), Data Acquisition Unit and Mapping Unit

Figure 6:
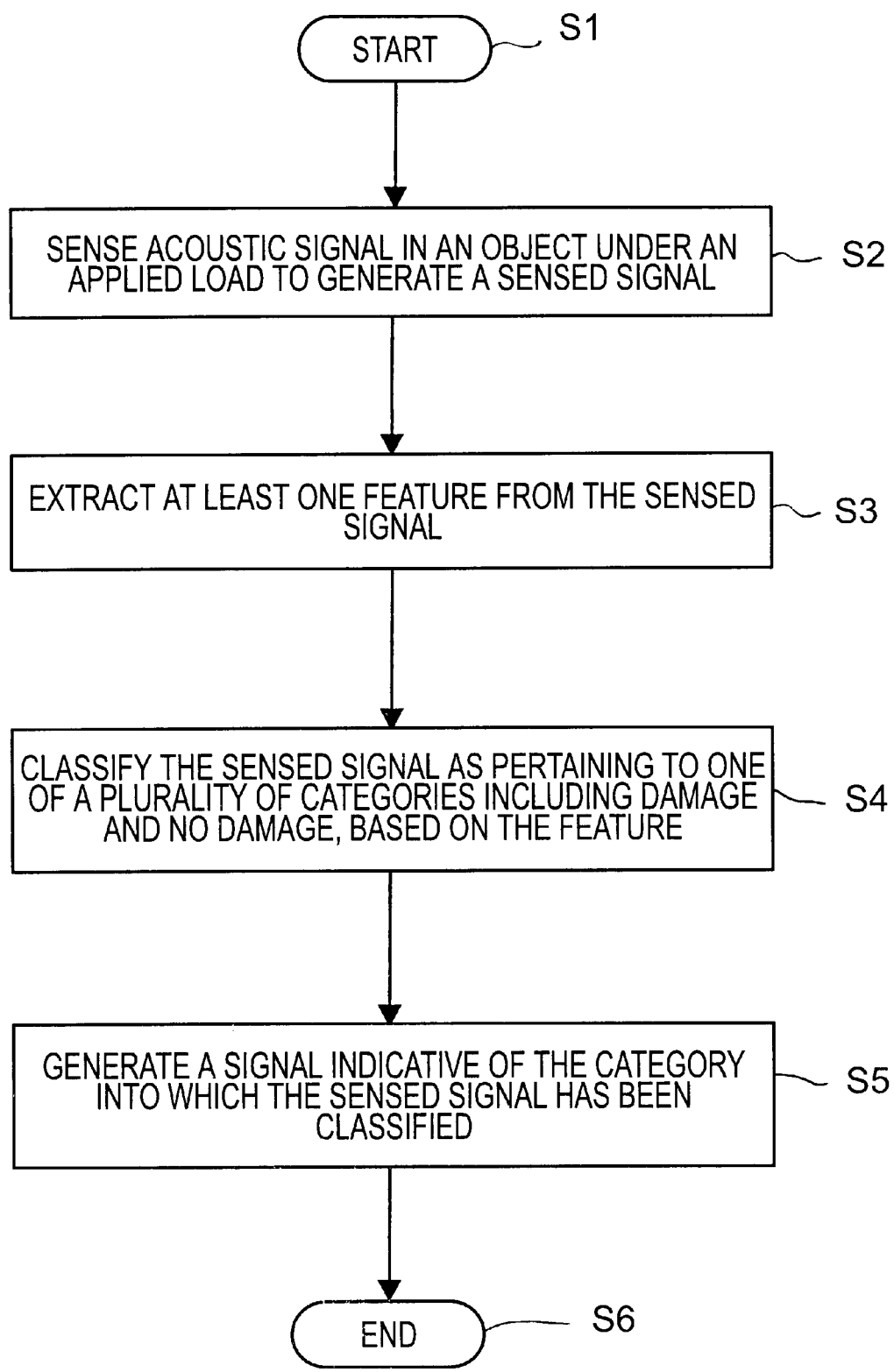
FIG. 6 is a flow chart of the general operation of the sensor and mapping unit of the invented apparatus, which also corresponds to a second method of this invention.

FIG. 6 is a basic flowchart of a method corresponding to the general operation of the apparatus 7 in sensing an acoustic signal, and classifying the acoustic signal as the result of damage, optionally of a particular type, or no damage to the object. In step S1 of FIG. 6, the method begins. In step S2, the apparatus 7 senses an acoustic signal from the object under an applied load, and generates a sensed signal based on the sensed acoustic signal. In step S3 of FIG. 6, the apparatus 7 extracts at least one feature from the sensed signal. In step S4 of FIG. 6, the apparatus classifies the sensed signal as pertaining to one of a plurality of categories including at least actual damage and no damage to the object, and also optionally damage of a particular type, based on the feature. In step S5 of FIG. 6, the apparatus generates a signal (i.e. damage data) indicative of the category into which the sensed signal has been classified, and in step S6 of FIG. 6, the method ends. The method of FIG. 6 is generally the same whether the apparatus 7 is operating in passive mode or active mode, the difference being that the passive mode classifies the damage as possible, as yet unconfirmed, damage in passive mode in step S4, and classifies the damage as actual damage in step S4 in the active mode.

6. An Exemplary Embodiment of the Feature Extraction Unit

Figure 4:
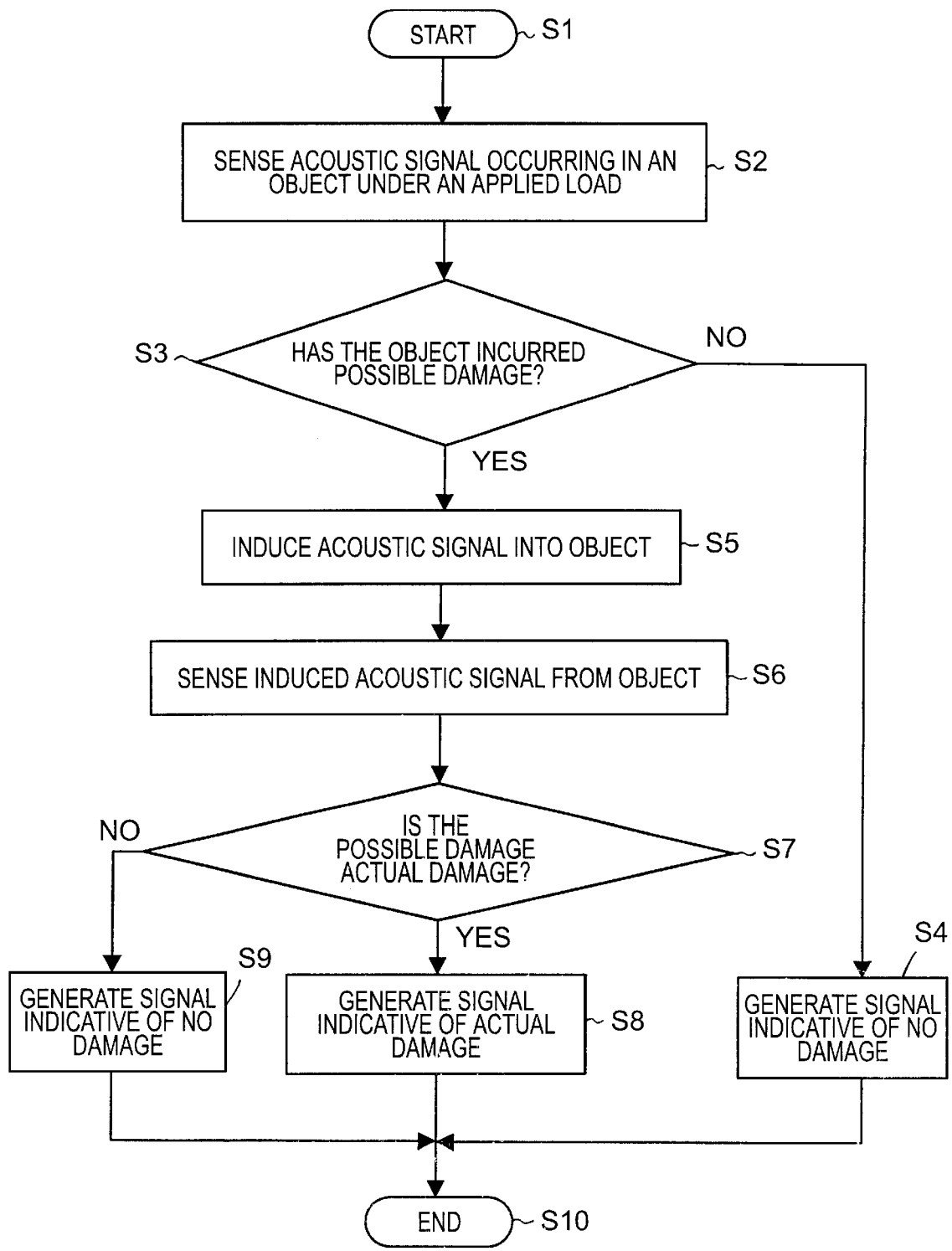
FIG. 4 is a flow chart of the general operation of the invented apparatus, which also depicts a first method of this invention.
Figure 7:
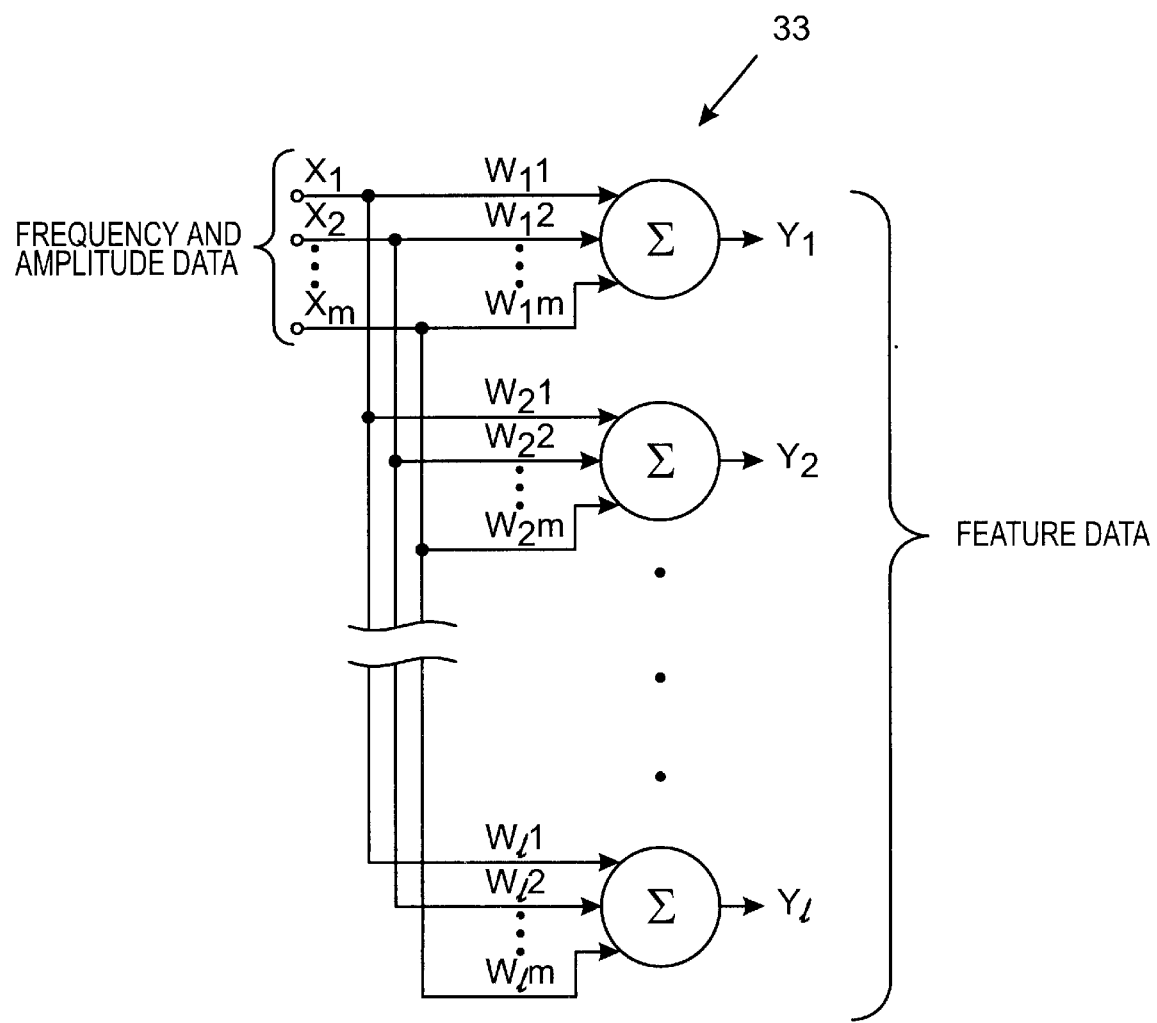
FIG. 7 is a diagram of a feature extraction unit included within the mapping unit, implemented as a neural network.

FIG. 7 is a diagram of an exemplary implementation of the feature extraction unit 33 included within the mapping unit 11. As shown in FIG. 4, the feature extraction unit 33 can be implemented as a neural network, in this case a one-dimensional lattice. A set of frequency and amplitude data $x_j$ from the data acquisition unit 14 are input to the feature extraction unit 33, which multiplies respective datum by weight factors $w_j$ and the resulting products are summed at the neurons to yield feature data $y_j$ (the boldface letters denote vectors). The feature extraction unit 33 is preferably implemented as a self-organizing map of the features In the training phase of the feature extraction unit 33, the weight factors $w_j$ can be selected at random and are preferably selected to be relatively small numbers. A sample set of frequency and amplitude data $x_j$ are input to the neurons, and the neuron whose weight factors $w_j$ most closely match the data $x_j$ (i.e. have the closest Euclidean distance) are determined. This criterion can be stated mathematically as:

$$i(x) = \arg \min_j \|x(n) - w_j\|, \ j = 1, 2, \ldots, l \quad (1)$$

where $i(x)$ is the winning neuron, that is, the neuron that is closest to the data $x_j$ in terms of Euclidean distance, n is an index for the present set of frequency and amplitude data $x_j$, and j is an index for the neurons, and l is the total number of neurons in the network. The next step in the training phase of the feature extraction unit 33 is to update the weight factors $w_j$ in preparation for the next or n+1st data set. This can be accomplished in accordance with the following equation:

$$w_j(n+1) = w_j(n) + \eta(n) h_{j,i(x)}(n)(x(n) - w_j(n)) \quad (2)$$

where $w_j(n+1)$ is the set of weight factors for the j neurons for the next or n+1st set of frequency and amplitude data, $w_j(n)$ is the set of weight factors used for the nth set of frequency and amplitude data, $\eta(n)$ is a learning rate parameter, and $h_{j,i(x)}$ is a neighborhood function centered on the winning neuron $i(x)$. The learning rate function can be:

$$\eta(n) = \eta_0 \exp(-n/\tau_1) \quad (3)$$

where $\eta_0$ and $\tau$ are predetermined constants. For example, the neighborhood function $h_{j,i(x)}(n)$ can be defined as:

$$h_{j,i(x)}(n) = \exp(-d^2_{j,i}/2\sigma^2(n)) \quad (4)$$

where $$d^2_{j,i} = \|r_j - r_i\|^2 \quad (5)$$

and $$\sigma(n) = \sigma_0 \exp(-n/\tau_2) \quad (6)$$

where $r_j$ is the lattice position of a neuron in the neighborhood of the winning neuron, $r_i$ is the lattice position of the winning neuron $i(x)$, and $\sigma_0$ and $\tau_2$ are predetermined constants. The above training steps are repeated for additional sets of frequency and amplitude data $x_j$ until no significant change is observed in the feature data $y_j$. Thereafter, in the operational phase of the apparatus 7, the feature extraction unit 33 performs to map the frequency and amplitude data $x_j$ from the data acquisition unit 14, to respective feature data $y_j$ that is output to the damage classification unit 34. Further details of the training phase are given in the aforementioned text.

7. An Exemplary Embodiment of the Damage Classification Unit

Figure 8:
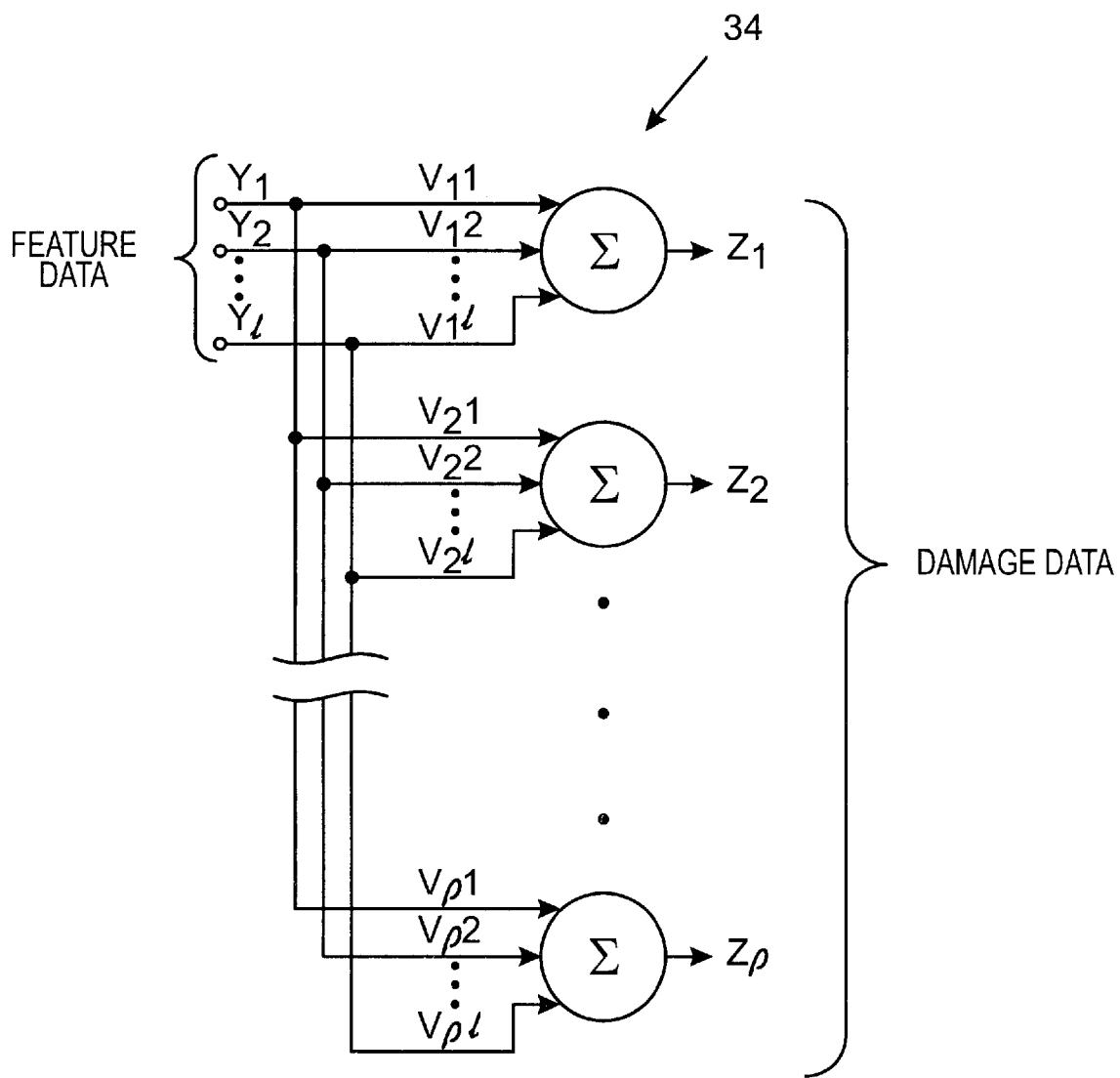
FIG. 8 is a diagram of a data classification unit included within the mapping unit, implemented as a neural network.

As shown in FIG. 8, the damage classification unit 34 can be implemented as a neural network that maps the feature data $y_j$ to corresponding damage data $z_j$. To train the damage classification unit 34 to properly perform this mapping, the following equation can be used if the damage classification unit 34 properly activates the neuron corresponding to the class of damage or no damage for the feature data $y_j$:

$$v_v(n+1) = v_v(n) + \alpha_n[y_j - v_v(n)] \quad (7)$$

where $v_v(n+1)$ is the Voronoi vector for the next or n+1st set of feature data $y_j$, $v_v(n)$ is the Voronoi vector that is closest to the feature data $y_j$, and $\alpha_n$ is a learning constant satisfying the relation $0 < \alpha_n < 1$. The effect of equation (7) is to move the Voronoi vector closer to the feature data $y_j$ if the damage classification unit 34 correctly classified the acoustic signal represented by the feature data $y_j$. On the other hand, if the damage classification unit 34 misclassifies the feature data $y_j$ into an incorrect classification as the damage data $z_j$, the Voronoi vector $v_v(n+1)$ is moved away from the feature data $y_j$ using the following equation:

$$v_v(n+1) = v_v(n) - \alpha_n[y_j - v_v(n)]. \quad (8)$$

The damage classification unit 34 is thus trained to map the feature data $y_j$ to damage data $z_j$ indicative of the appropriate damage or no damage classification so that the damage classification unit 34 performs appropriately in the operational mode of the apparatus 7.

8. Processing Performed by the Controller

FIGS. 9A–9D are flowcharts of processing performed by the controller 12. In step S1 of FIG. 9A, the processing performed by the controller 12 begins. Initially, the controller 12 is in the passive mode of operation. In step S2, the controller 12 receives damage data from the damage classification unit 34, or more generally, the mapping unit 11. In step S3, the controller 12 determines whether the damage data indicates that the object has incurred possible damage. If so, the controller 12 switches from passive mode to active mode, and processing proceeds to step S4 in which the controller 12 retrieves predetermined induced signal data from the memory 16. Such predetermined induced signal data can be stored in the memory 16 via the input unit 19 and the controller 12 before operation of the apparatus 7. The controller 12 supplies the retrieved induced signal data to the signal generation unit 15. In step S5, the controller 12 receives the damage data resulting from the induced acoustic signal in the object 1, and in step S6, the controller 12 determines whether the possible damage is actual damage to the object. If so, the controller 12 returns to the passive mode, and the controller 12 retrieves a damage count from the memory 16 in step S7 of FIG. 9B (the damage count is initialized to zero before the start of operation of the apparatus 7). In step S8, the controller 12 increments the retrieved damage count. In step S9, the controller 12 stores the incremented damage count in the memory 16. In step S10, the controller 12 retrieves a predetermined damage limit from the memory 16 that can be stored in the memory 16 before operation of the apparatus 7 via the input unit 19 and the controller, for example, and compares the incremented damage count with the retrieved predetermined damage limit. If the incremented damage count exceeds the predetermined damage limit, the controller 12 generates an alarm signal in step S12 and supplies the alarm signal to the alarm unit 17 to alert the user of the apparatus 7 that the object 1 has been damaged beyond the predetermined damage limit. After performance of step S12 or if the determination in step S11 is negative, processing proceeds to step S13 of FIG. 9C in which the controller receives the time data and amplitude data from the data acquisition unit 14. In step S14, the controller 12 generates a display signal based on the received time data and amplitude data, and supplies the display signal to the display unit 18 to generate a visual display showing the location and/or the extent of damage incurred by the object 1. In step S15 of FIG. 9C, the controller 12 stores the damage data, optionally with the time data and amplitude data, and further as an option with the applied load data, in the memory 16. The data stored in step S15 constitute record data which is a log of the damage incurred by the object 1 under the applied load 20. After negative determinations in steps S3 or S6, or after the performance of step S15, processing performed by the controller 12 proceeds to step S16. It should be noted that the controller 12 switches the apparatus from active mode to passive mode after the performance of step S6 whether the determination in step S6 is affirmative or negative. In step S16, the controller 12 determines whether the user has requested the controller 12 to display the record data. If so, in step S17, the controller 12 retrieves the record data from the memory 16, generates a display signal based thereon, and supplies the display signal to the display unit 18 to generate a visual display that can be observed by the user. If the determination in step S16 is negative or after the performance of step S17, processing performed by the controller 12 proceeds to step S18 of FIG. 9D. In step S18, the controller 12 retrieves applied load data from the memory 16. The applied load data 16 is initially set to a predetermined initial load by the user via the input unit 19 and the controller 12, for example. In step S19, the controller 12 retrieves a predetermined applied load increment from the memory 16 that can be initialized by the user before operation of the apparatus 7 via the input unit 19 and the controller 12. In step S19, the controller 12 increments the retrieved applied load data by the retrieved increment. In step S20, the controller 12 supplies the incremented applied load data to the load applicator 50. In step S21, the controller 12 stores the incremented applied load data in the memory 16, and in step S22, the processing performed by the controller 12 ends. The controller 12 preferably repeats the processing of FIGS. 9A–9D at intervals of, for example, one or two milliseconds or less.

9. Variations of the Invented Apparatus and Methods

FIG. 10 shows a variation of the invented apparatus 7 in which the feature extraction unit 33 is divided into two portions 60, 61, one for the passive mode and one for the active mode, which can be implemented with respective neural networks and trained with respective data sets in a manner similar to that previously explained. Also, in this variation, the damage classification unit 34 is divided into two portions 62, 63 that are coupled to receive feature data from respective feature extraction unit portions 60, 61, and that generate respective damage data based thereon. The portions 62, 63 can be trained with respective data sets in a manner similar to that previously explained herein. So that the controller 12 can control the flow of feature data to the proper one of the portions 60, 62 or portions 61, 63 in accordance with whether the apparatus 7 is in passive mode or active mode, respectively, in this variation, the apparatus 7 includes a demultiplexer (DEMUX) 54 coupled between the data acquisition unit 14 and the portions 60, 61 of the feature extraction unit 33. The DEMUX 54 is also coupled to receive at its control terminal a switch signal generated by the controller 12. The DEMUX 54 supplies the feature data from the data acquisition unit 14 to one of the portions 60, 61, based on the state of the switch signal. The controller 12 can switch the state of the switch signal from passive mode to active mode after an affirmative determination in step S3 of FIG. 9A, and can switch back to passive mode after either an affirmative or negative determination as a result of the performance of step S6 in FIG. 9A. The apparatus 7 can further include a multiplexer (MUX) 65 coupled between the portions 62, 63 and the controller 12, and further coupled to receive the switch signal from the controller at its control terminal. The multiplexer 65 supplies the damage data from either the portions 62, 63 to the controller 12, based on the state of the switch signal generated by the controller.

It should be noted that the load applicator 50 is an optional element of the invented apparatus, and can be omitted in particular applications. For example, the apparatus 7 without the load applicator 50 could be integrated with an object 1 constituting a panel or portion of an aircraft or other structure, and can be used as a so-called smart material to indicate whether stress applied from flight dynamics is approaching the structure's failure point, for example. This possibility of use of the apparatus 7 and disclosed methods is intended to be included within the scope of this invention.

Figure 9B:
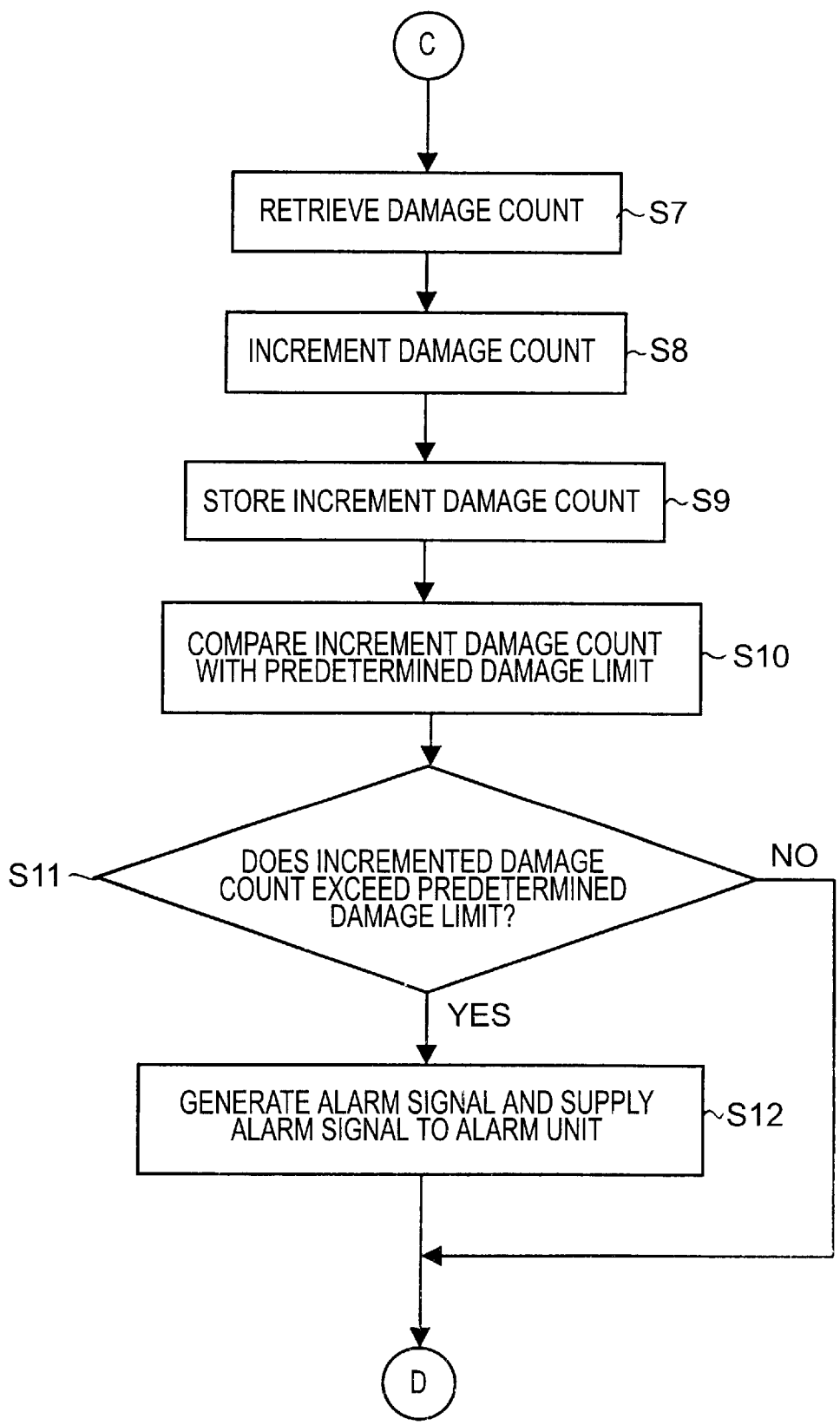
Figure 9C:
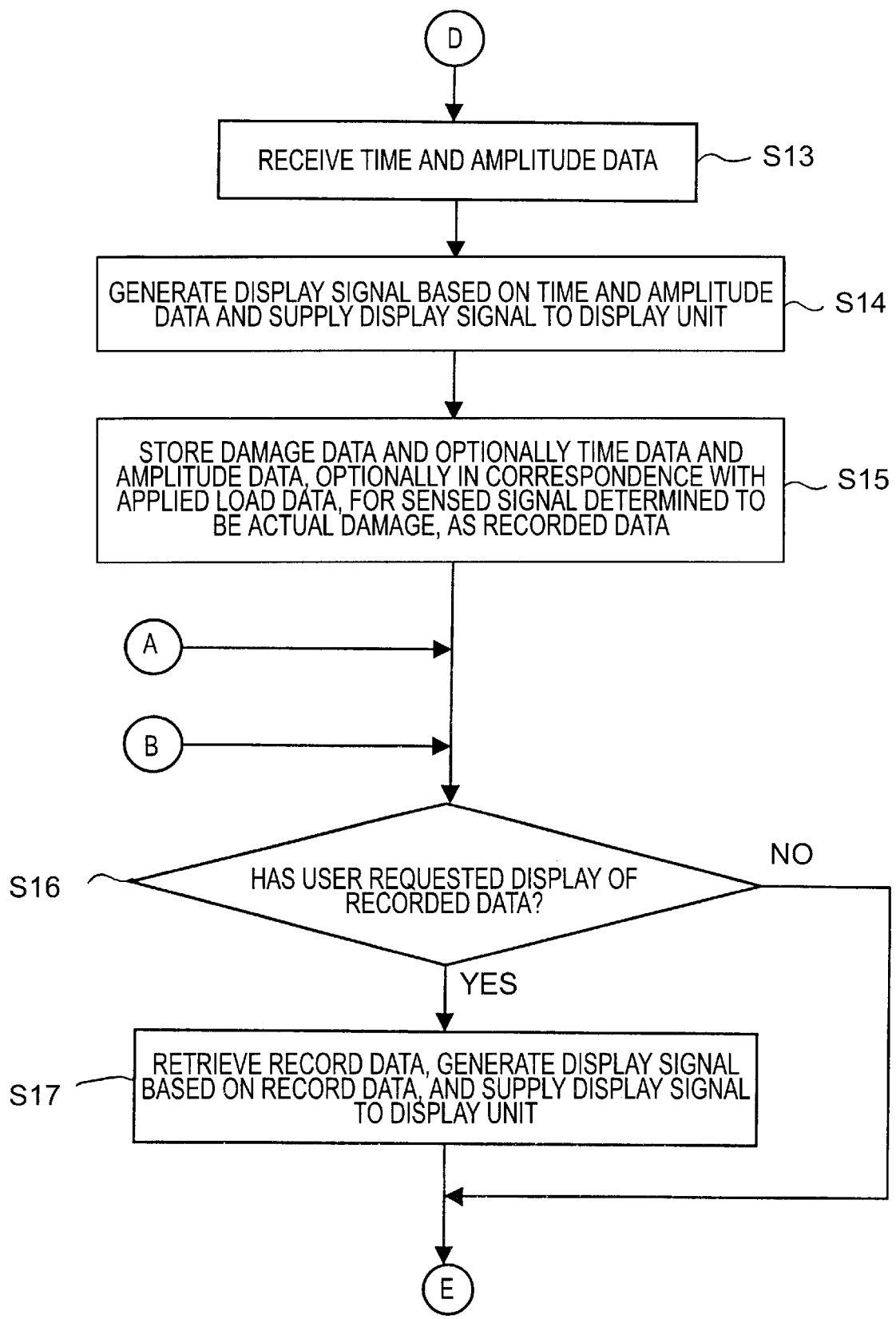
Figure 9D:
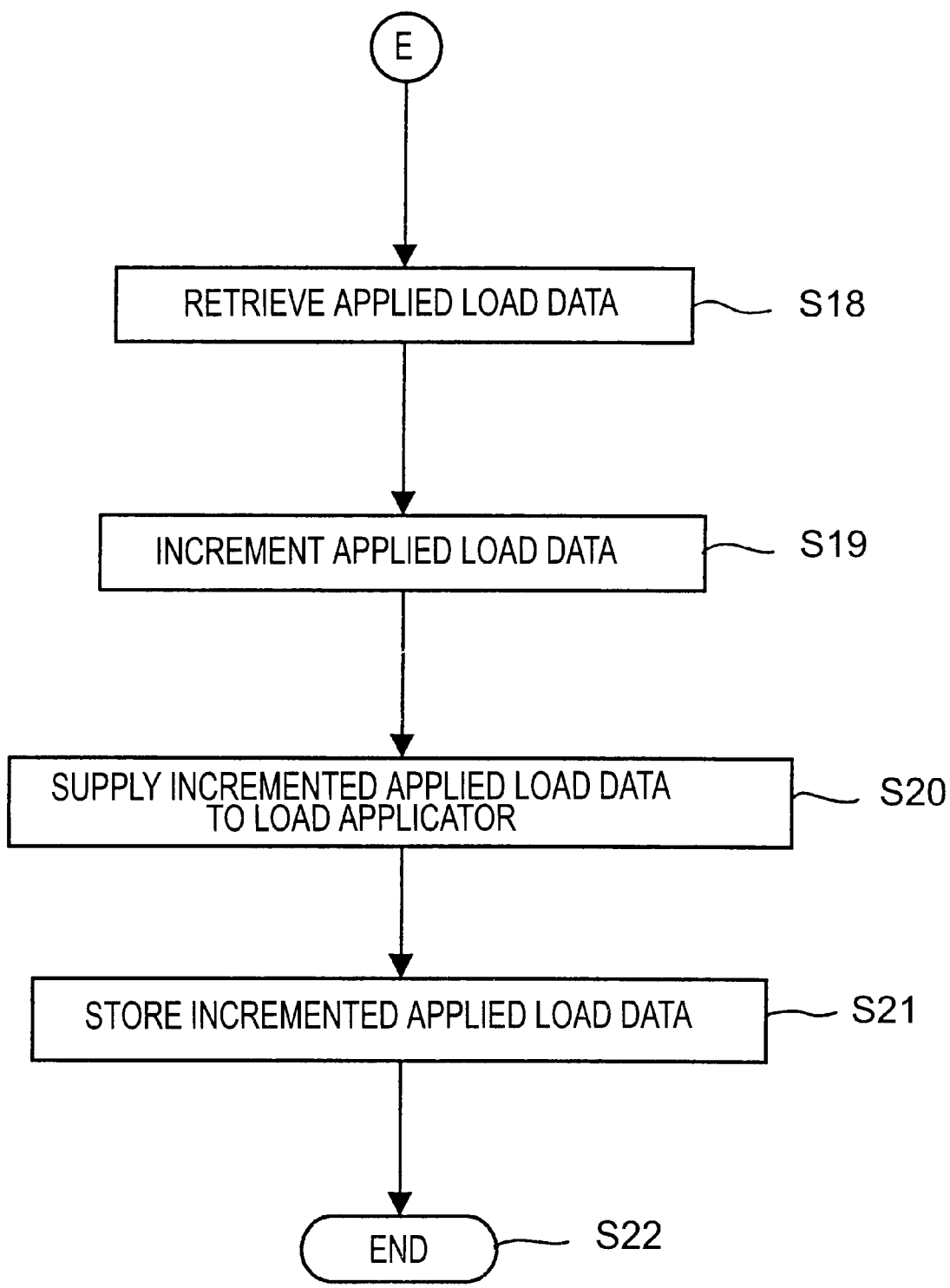

Steps S7–S10 of FIG. 9B could be repeated for different categories of damage. For example, excessive damage to the object in any one category could be the basis to trigger an alarm in steps S11 and S12. For example, excessive damage to the object in categories such as fiber damage, fiber-matrix interface damage, fiber-matrix debonding, or matrix damage in the case of a composite material, could be the basis to trigger an alarm in steps S11 and S12. In the case of an object 1 composed of a monolithic material, excessive damage to the object in categories such as surface cracking, necking, fatigue, and/or cracking, could be used to trigger the alarm in steps S11 and S12. Similarly, in steps S13–S17 of FIG. 9C, record data could be stored and/or displayed by damage classification.

In the following claims, "acoustic inspection means" refers to the apparatus 7 for purposes of 35 U.S.C. §112, Sixth Paragraph. Those claims that do not specifically recite "means" are not intended to be interpreted as recited in means plus function form under 35 U.S.C. §112, Sixth Paragraph.

The many features and advantages of the present invention are apparent from the detailed specification and thus, it is intended by the appended claims to cover all such features and advantages of the described apparatus and methods which follow in the true spirit and scope of the invention. Further, since numerous modifications and changes will readily occur to those of ordinary skill in the art, it is not desired to limit the invention to the exact construction and operation illustrated and described. Accordingly, all suitable modifications and equivalents may be resorted to as falling within the spirit and scope of the invention.

What is claimed is:

1. A method comprising the steps of:
   a) sensing at least one acoustic signal occurring in an object under an applied load;
   b) determining whether the object has incurred possible damage under the applied load, based on the acoustic signal sensed in said step (a);
   c) inducing at least one acoustic signal in the object if said step (b) indicates that the object has incurred possible damage, the induced acoustic signal encountering at least the portion of the object that has incurred possible damage;
   d) sensing the induced acoustic signal from the object; and
   e) determining whether the possible damage is actual damage of the object, based on the induced acoustic signal sensed in said step (d).

2. A method as claimed in claim 1, wherein said step (b) includes the substep of:
   b1) classifying the acoustic signal sensed in said step (a) as pertaining to one of a plurality of categories including at least possible damage to the object and no damage to the object, based on the acoustic signal sensed in said step (a).

3. A method as claimed in claim 2, wherein said step (b) includes the substep of:
   b2) extracting at least one feature from the acoustic signal sensed in said step (a) for use in the performance of the classifying in the substep (b1).

4. A method as claimed in claim 2, wherein said step (b) includes the substep of:
   b2) before performing the substep (b1), training a learning system to classify a predetermined set of sensed acoustic signals into the categories including at least possible damage and no damage,
   the substep (b1) being performed by the learning system.

5. A method as claimed in claim 4, wherein the learning system includes a neural network.

6. A method as claimed in claim 2, wherein a sensed signal is generated in said step (a), based on the acoustic signal sensed in said step (a), the method further comprising the steps of:
   f) sampling the sensed signal to generate time and amplitude data; and
   g) converting the time and amplitude into frequency and amplitude data, the substep (b1) performed using the frequency and amplitude data.

7. A method as claimed in claim 2, wherein the object is a composite material including fiber and matrix layers, and wherein the classifying of the substep (b1) is performed to further classify the possible damage to the object into possible fiber damage, possible fiber-matrix interface damage, possible fiber-matrix debonding, and possible matrix damage, said step (b) determining that the object has incurred possible damage if the damage is classified in said step (b1) as possible fiber damage, possible fiber-matrix interface damage, possible fiber-matrix debonding, and possible matrix damage.

8. A method as claimed in claim 7, wherein the substep (b1) further classifies the possible fiber damage into possible damage for respective fiber layers.

9. A method as claimed in claim 2, wherein the object is a monolithic material, and wherein the classifying of the substep (b1) is performed to further classify the possible damage into possible surface cracking, possible necking, possible fatigue, and possible cracking.

10. A method as claimed in claim 1, wherein said step (e) includes the substeps of:
    e1) classifying the induced acoustic signal sensed in said step (d) as pertaining to one of a plurality of categories including at least actual damage and no damage.

11. A method as claimed in claim 10, wherein said step (e) includes the substep of:
    e2) extracting at least one feature from the acoustic signal sensed in said step (d) for use in the performance of the classifying in the substep (e1).

12. A method as claimed in claim 10, wherein said step (e) further includes the substep of:
    e2) before performing the substep (e1), training a learning system to classify a predetermined set of induced acoustic signals into categories including at least actual damage and no damage,
    the substep (e1) being performed by the learning system.

13. A method as claimed in claim 12, wherein the learning system includes a neural network.

14. A method as claimed in claim 10, wherein a sensed signal generated in said step (c) based on the induced acoustic signal sensed in said step (d), the method further comprising the steps of:
    f) sampling the sensed signal to generate time and amplitude data; and
    g) converting the time and amplitude into frequency and amplitude data, the substep (e1) performed using the frequency and amplitude data.

15. A method as claimed in claim 14, further comprising the step of:
    h) storing at least one of the amplitude data, time data, and applied load data, in a memory in correspondence with the category of actual damage for the acoustic signal as classified in the substep (e1).

16. A method as claimed in claim 10, wherein the object is a composite material including fiber and matrix layers, and wherein the classifying of the substep (e1) is performed to further classify the possible object damage into actual fiber damage, actual fiber-matrix interface damage, actual fiber-matrix debonding, and actual matrix damage, said step (e) determining that the object has incurred actual damage if the possible damage is classified in said step (e1) as actual fiber damage, actual fiber-matrix interface damage, actual fiber-matrix debonding, and actual matrix damage.

17. A method as claimed in claim 16, wherein the substep (e1) further classifies the actual fiber damage into actual fiber damage for respective fiber layers.

18. A method as claimed in claim 16, further comprising the step of:
f) incrementing an actual matrix damage count if said step (e1) classifies the possible damage as actual matrix damage;
g) comparing the actual matrix damage count with a predetermined matrix damage count value; and
h) generating an alarm, based on said step (g).

19. A method as claimed in claim 16, further comprising the step of:
f) incrementing an actual fiber damage count if said step (e1) classifies the damage actual fiber damage;
g) comparing the actual fiber damage count with a predetermined fiber damage count value; and
h) generating an alarm, based on said step (g).

20. A method as claimed in claim 16, further comprising the step of:
f) incrementing an actual fiber-matrix interface damage count if said step (e1) classifies the possible damage as actual fiber-matric interface damage;
g) comparing the actual fiber-matrix interface damage count with a predetermined fiber-matrix interface damage value; and
h) generating an alarm, based on said step (g).

21. A method as claimed in claim 16, further comprising the step of:
f) incrementing an actual fiber-matrix debonding damage count if said step (e1) classifies the possible damage as actual fiber-matrix debonding damage;
g) comparing the actual matrix damage count with a predetermined fiber-matrix debonding damage count value; and
h) generating an alarm, based on said step (g).

22. A method as claimed in claim 10, wherein the object is a monolithic material, and wherein the classifying the actual damage in the substep (e1) into actual surface cracking, actual necking, actual fatigue, and actual cracking.

23. A method as claimed in claim 16, further comprising the step of:
f) incrementing an actual surface cracking damage count if said step (e1) classifies the possible damage as actual matrix damage;
g) comparing the actual surface cracking damage count with a predetermined actual surface cracking damage count value; and
h) generating an alarm, based on said step (g).

24. A method as claimed in claim 16, further comprising the step of:
f) incrementing an actual necking damage count if said step (e1) classifies the damage actual necking damage;
g) comparing the actual necking damage count with a predetermined actual necking damage count value; and
h) generating an alarm, based on said step (g).

25. A method as claimed in claim 16, further comprising the step of:
f) incrementing an actual fatigue damage count if said step (e1) classifies the possible damage as actual fatigue damage;
g) comparing the actual fatigue damage count with a predetermined actual fatigue damage value; and
h) generating an alarm, based on said step (g).

26. A method as claimed in claim 16, further comprising the step of:
f) incrementing an actual cracking damage count if said step (e1) classifies the possible damage as actual cracking damage;
g) comparing the actual cracking damage count with a predetermined actual cracking damage count value; and
h) generating an alarm, based on said step (g).

27. A method as claimed in claim 1, further comprising the step of:
f) generating a display of the actual damage, if any, determined in said step (e).

28. A method as claimed in claim 27, wherein said step (b) determines the location of the actual damage in the object, and wherein the display is generated in said step (f) to include the location of the actual damage.

29. A method as claimed in claim 27, wherein said step (b) determines the extent of the possible damage in the object, and wherein the display is generated in said step (f) to include the extent of the actual damage.

30. A method as claimed in claim 1, further comprising the step of:
f) generating an alarm if the object is determined to have actual damage in said step (e).

31. A method as claimed in claim 1, wherein said steps (a) through (e) are repeatedly performed.

32. A method as claimed in claim 31, further comprising the step of:
f) tracking the amount of actual damage incurred by the object;
g) determining whether the amount of actual damage has exceeded a predetermined amount of damage; and
h) generating an alarm, based on the determination of said step (g).

33. A method as claimed in claim 31, further comprising the step of:
f) incrementing the load applied to the object after each performance of said step (e) and before subsequent performance of said step (a).

34. A method comprising the steps of:
a) sensing at least one acoustic signal occurring in an object under an applied load, and generating a signal indicative of the sensed acoustic signal;
b) sampling the signal indicative of the acoustic signal sensed in said step (a) to generate time and amplitude data;
c) converting the time and amplitude data of said step (b) into frequency and amplitude data;
d) classifying the frequency and amplitude data converted in said step (c), as pertaining to one of a plurality of categories including at least possible damage and no damage;
e) inducing at least one acoustic signal into the object if said step (d) indicates that the object has incurred possible damage, the induced acoustic signal encountering at least the portion of the object that has incurred possible damage;

f) sensing the acoustic signal induced in said step (e), and generating a signal indicative of the sensed acoustic signal induced in said step (e);

g) sampling the signal indicative of the acoustic signal sensed in said step (f) to generate time and amplitude data;

h) converting the time and amplitude data of said step (g) into frequency and amplitude data; and i) classifying the frequency and amplitude data converted in said step (h), as pertaining to one of a plurality of categories including at least actual damage and no damage.

35. A method as claimed in claim 34, further comprising the step of:

j) extracting at least one feature from the frequency and amplitude data of said step (c) for use in the performance of said step (d).

36. A method as claimed in claim 34, further comprising the step of:

j) extracting at least one feature from the frequency and amplitude data of said step (h) for use in the performance of said step (i).

37. A method as claimed in claim 34, further comprising the step of:

j) training a learning system to perform the classifying of said step (d) with a predetermined set of frequency and amplitude data derived from acoustic signals and corresponding categories.

38. A method as claimed in claim 34, further comprising the step of:

j) training a learning system to perform the classifying of said step (i) with a predetermined set of frequency and amplitude data derived from acoustic signals and corresponding categories.

39. A method as claimed in claim 34, wherein said steps (a) through (i) are repeatedly performed.

40. A method as claimed in claim 39, further comprising the steps of:

j) tracking the amount of actual damage incurred by the object;

k) determining whether the amount of actual damage has exceeded a predetermined amount of damage; and l) generating an alarm, based on the determination of said step (k).

41. A method as claimed in claim 34, further comprising the steps of:

j) recording the category of actual damage classified in said step (i) in correspondence with at least one of the time data, amplitude data, and applied load data indicative of the amount and direction of the applied load.

42. A method as claimed in claim 34, further comprising the step of:

j) displaying the object and any actual damage thereof.

43. A method as claimed in claim 34, further comprising the step of:

j) amplifying the signal indicative of the acoustic signal sensed in said step (a), before performing said step (b).

44. A method as claimed in claim 34, further comprising the step of:

j) analog-to-digital converting the signal indicative of the acoustic signal sensed in said step (a), before performing said step (b).

45. A method as claimed in claim 34, further comprising the step of:

j) generating a signal for the acoustic signal induced in said step (e), said step (e) including the substep of transducing the signal generated in said step (j) to induce the acoustic signal in the object.

46. A method as claimed in claim 45, wherein the signal generated in said step (j) is in digital form, the method further comprising the step of:

k) digital-to-analog converting the signal generated in said step (j) into an analog signal before transducing the analog signal in the performance of said step (e).

47. A method as claimed in claim 46, further comprising the step of:

k) amplifying the signal generated in said step (j) before transducing the amplified signal in the performance of said step (e).

48. A method as claimed in claim 34, further comprising the step of:

j) amplifying the signal indicative of the acoustic signal sensed in said step (f), before the performance of said step (g).

49. A method as claimed in claim 34, further comprising the step of:

j) analog-to-digital converting the signal indicative of the acoustic signal sensed in said step (f), before performing said step (g).

50. An apparatus for detecting damage to an object under an applied load, the apparatus comprising:

acoustic inspection means operatively coupled to the object, the acoustic inspection means having passive and active modes of operation, in the passive mode, the acoustic inspection means sensing at least one acoustic signal occurring in the object under the applied load to determine whether the object has incurred possible damage, the acoustic inspection means switching from passive mode to active mode if the object has incurred possible damage, and remaining in passive mode if the object has incurred no damage; and in the active mode, the acoustic inspection means inducing at least one acoustic signal into the object to probe the possible damage in the object, the acoustic inspection means sensing the induced acoustic signal from at least a portion of the object having possible damage, and determining whether the possible damage is actual damage of the object, based on the sensed acoustic signal, the acoustic inspection means generating a signal indicative of the actual damage of the object, based on the sensed acoustic signal, and returning to the passive mode after generating the signal indicative of the actual damage of the object.

51. An apparatus as claimed in claim 50, wherein the acoustic inspection means extracts at least one feature from the acoustic signal sensed in the passive mode and classifies the acoustic signal as possible damage or no damage, based on the extracted feature.

52. An apparatus as claimed in claim 50, wherein the acoustic inspection means transduces the acoustic signal sensed in the passive mode into a signal indicative thereof, the acoustic inspection means sampling the signal indicative of the acoustic signal sensed in the passive mode to generate time and amplitude data, the acoustic inspection means converting the time and amplitude data into frequency and amplitude data from which the acoustic inspection means extracts the feature.

53. An apparatus as claimed in claim 50, wherein the acoustic inspection means extracts at least one feature from the acoustic signal sensed in the active mode and classifies the acoustic signal sensed in the active mode as actual damage or no damage, based on the extracted feature.

54. An apparatus as claimed in claim 50, wherein the acoustic inspection means transduces the acoustic signal sensed in the active mode into a signal indicative of the acoustic signal, the acoustic inspection means sampling the signal indicative of the acoustic signal sensed in the active mode to generate time and amplitude data, the acoustic inspection means converting the time and amplitude data into frequency and amplitude data from which the acoustic inspection means extracts the feature.

55. An apparatus as claimed in claim 50, wherein the acoustic inspection means switches from passive mode to active mode, and from active mode back to passive mode, to evaluate each acoustic signal sensed by the acoustic inspection means.

56. An apparatus as claimed in claim 50, wherein the acoustic inspection means tracks the amount of actual damage incurred by the object, compares the amount of actual damage to a predetermined damage amount, and generates an alarm if the actual damage amount exceeds the predetermined damage amount.

57. An apparatus as claimed in claim 50, wherein the acoustic inspection means generates a visual display to indicate the location and extent of object damage, based on the signal indicative of the actual damage.

58. An apparatus as claimed in claim 50, wherein the acoustic inspection means generates and transduces a signal to induce the acoustic signal in the object in the active mode.

59. An apparatus for detecting damage to an object under an applied load, the apparatus comprising:
   at least one sensor mounted to sense an acoustic signal from the object, and generating a sensed signal, based on the sensed acoustic signal;
   a mapping unit coupled to the sensor, for generating damage data indicative of possible damage in a passive mode of operation of the apparatus, based on the sensed signal, and for generating damage data indicative of actual damage incurred by the object in an active mode of operation of the apparatus, based on the sensed signal;
   a controller coupled to the mapping unit, the controller restricting the apparatus to the passive mode if the damage data indicates that an object has incurred no damage a processor for switching the apparatus from the passive mode to the active mode to generate induced signal data to induce at least one acoustic signal in the object if the damage data indicates that the object has incurred possible damage, the processor determining whether the possible damage is actual damage to the object or no damage, based on the damage data corresponding to the induced acoustic signal, the processor switching an apparatus from the active mode to passive mode after making the determining of whether the possible damage is actual damage or no damage; and
   a transducer coupled to the controller and mounted to the object, the transducer inducing the acoustic signal in the object based on the induced signal data.

60. An apparatus as claimed in claim 59, further comprising;
   a data acquisition unit coupled to the sensor, the data acquisition unit sampling the sensed signal to generate time and amplitude data, and converting the time and amplitude data in time domain, to frequency and amplitude data in frequency domain, the data acquisition unit supplying the frequency and amplitude data to the mapping unit.

61. An apparatus as claimed in claim 60, wherein the data acquisition unit includes
   an amplifier coupled to the sensor, for amplifying the sensed signal to generate an amplified signal;
   an analog-to-digital converter coupled to the amplifier, for converting the amplified signal into a digital signal; and
   a digital signal processor coupled to the analog-to-digital converter, the digital signal processor generating a sampling signal supplied to the analog-to-digital converter to cause the analog-to-digital converter to sample amplitude of the amplified signal at regular time increments, the digital signal processor receiving the amplitudes in association with respective time increments to generate time and amplitude data, the digital signal processor converting the time and amplitude data in time domain, to frequency and amplitude data in frequency domain, the digital signal processor supplying the frequency and amplitude data to the feature extraction unit.

62. An apparatus as claimed in claim 60 wherein the mapping unit includes
   a feature extraction unit coupled to the data acquisition unit, the feature extraction unit extracting at least one feature from the frequency and amplitude data; and
   a damage classification unit coupled to receive the feature from the feature extraction unit, and generating the damage data to indicate whether the object has incurred possible damage in the apparatus' passive mode of operation, based on the extracted feature, and for generating the damage data to indicate whether the object has incurred actual damage in the apparatus active mode of operation, based on the extracted feature.

63. An apparatus as claimed in claim 59, further comprising:
   a signal generation unit coupled between the processor and a transducer, the signal generation unit generating an induced signal, based on the induced signal data, that is transduced into the induced acoustic signal by the transducer.

64. An apparatus as claimed in claim 59, further comprising:
   a memory coupled to the controller, for storing at least one count for the amount of actual damage incurred by the object.

65. An apparatus as claimed in claim 64 further comprising;
   an alarm unit coupled to the controller, the controller comparing at least one count stored in the memory with a respective predetermined damage limit value, the controller generating an alarm signal supplied to the alarm unit if the count exceeds the predetermined damage limit value.

66. An apparatus as claimed in claim 59, wherein the object includes a composite material having matrix and fiber materials, and the damage data includes a plurality of categories including possible fiber damage, possible fiber-matrix interface damage, possible fiber-matrix debonding, possible matrix damage, and no damage in the passive mode, and the damage classification data includes a plurality of categories including actual fiber damage, actual fiber-matrix interface damage, actual fiber-matrix debonding, actual matrix damage, actual fiber damage, and no damage in the active mode.

67. An apparatus as claimed in claim 66, wherein the fiber damage class for the passive mode and the active mode is further divided into fiber layer damage for actual damage to respective fiber layers of the composite material.

68. An apparatus as claimed in claim 59, wherein the object includes a monolithic material, and the damage data includes a plurality of categories including possible surface cracking, possible necking, possible fatigue, possible cracking, and no damage in the passive mode, and the damage classification data includes a plurality of categories including actual surface cracking, actual necking, actual fatigue, actual cracking, and no damage in the active mode.

69. An apparatus as claimed in claim 60 has an acoustic inspection unit which includes:

a display unit coupled to the controller, the controller coupled to receive the time and amplitude data from a pulsating of sensors mounted at spaced positions to the object from the data acquisition unit, the controller generating a display signal supplied to the display unit to generate a visual display, based on the time and amplitude data from the plurality of sensors.

70. An apparatus as claimed in claim 59, wherein the controller includes a microprocessor.

* * * * *